US007980118B2

(12) United States Patent
He et al.

(10) Patent No.: US 7,980,118 B2
(45) Date of Patent: Jul. 19, 2011

(54) SYSTEM AND METHOD FOR ESTIMATING APPARENT VISCOSITY OF A NON-NEWTONIAN FLUID

(75) Inventors: Canlong He, St. Peters, MO (US); Paul G. Conley, St. Charles, MO (US)

(73) Assignee: Lincoln Industrial Corporation, St. Louis, MO (US)

( * ) Notice: Subject to any disclaimer, the term of this patent is extended or adjusted under 35 U.S.C. 154(b) by 690 days.

(21) Appl. No.: 12/130,700

(22) Filed: May 30, 2008

(65) Prior Publication Data
US 2009/0293594 A1    Dec. 3, 2009

(51) Int. Cl.
*G01N 11/04* (2006.01)
*G01N 11/06* (2006.01)

(52) U.S. Cl. .............. 73/54.06; 73/54.09; 73/54.01; 73/54.13

(58) Field of Classification Search ............... 73/53.05, 73/54.01, 54.04, 54.05, 54.06, 54.07, 54.08, 73/54.09, 54.11, 54.12, 54.13, 54.14
See application file for complete search history.

(56) References Cited

OTHER PUBLICATIONS

ASTM-D-1092. "Standard Test Method for Measuring Apparent Viscosity of Lubricating Greases." Nov. 2005.*
Conley, Centralized Lubrication Systems and Associated Grease Behavior, Chicago Section STLE, Feb. 17, 2005, 19 pages, United States.
Rotter, The Lincoln Ventmeter and Its Possibilities, NLGI 32nd Annual, Oct. 1964, pp. 268-273, Chicago, Illinois.
Conley, Lincoln Ventmeter Provides Invaluable Information in Addition to Aiding Lubrication System Design, NGLI, Dec. 2007, pp. 17-21, Lake Buena Vista, Florida.
Conley, An Update on the Lincoln Ventmeter, NLGI, Oct. 1964, 10 pages, United States.

* cited by examiner

*Primary Examiner* — Lisa M Caputo
*Assistant Examiner* — Punam Roy
(74) *Attorney, Agent, or Firm* — Senniger Powers LLP

(57) ABSTRACT

Method and apparatus for estimating an apparent viscosity of a non-Newtonian fluid. The results may be used for selecting equipment for pumping systems.

30 Claims, 19 Drawing Sheets

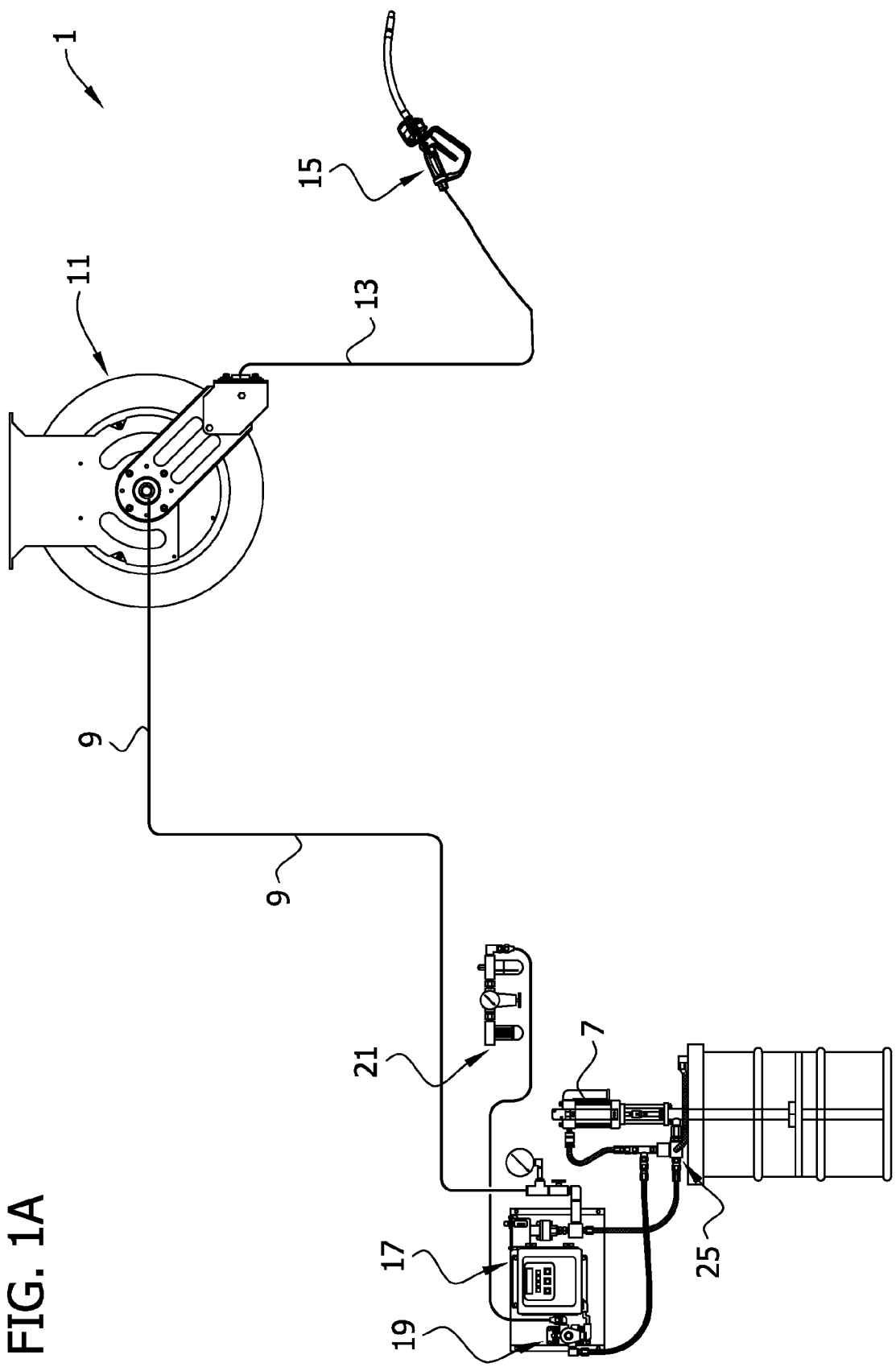

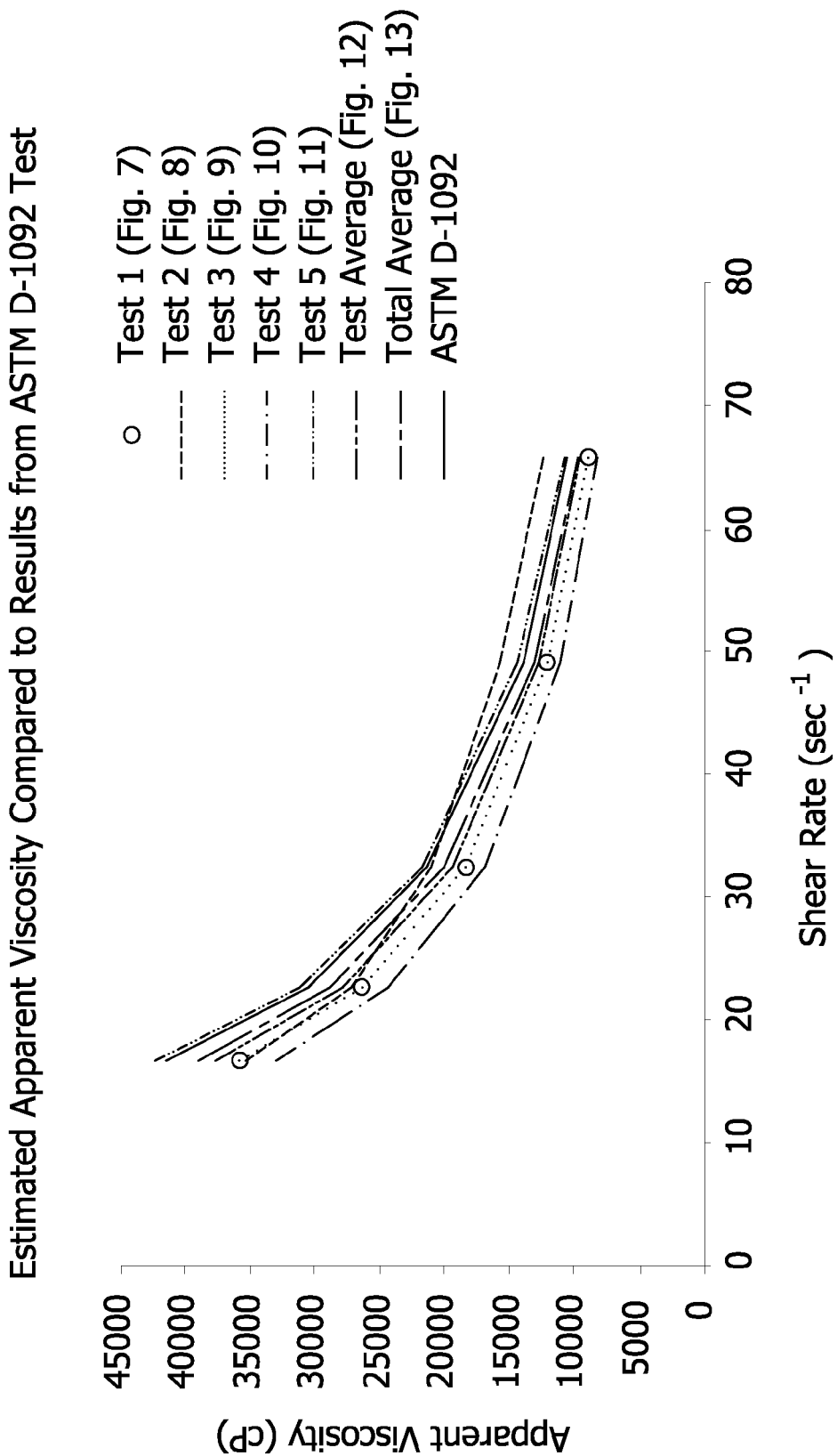

SYSTEM AND METHOD FOR ESTIMATING APPARENT VISCOSITY OF A NON-NEWTONIAN FLUID

FIELD OF THE INVENTION

The present invention generally relates to a system, apparatus and a method for estimating the apparent viscosity of a non-Newtonian fluid, such as lubrication greases, inks and adhesives. This information is useful in designing fluid flow systems, such as (but not limited to) fluid dispensing systems and lubrication systems.

BACKGROUND OF THE INVENTION

Apparent viscosity has been accepted increasingly by design engineers in sizing pumps and other components of fluid flow systems, such as grease lubrication systems. In general, the apparent viscosity of a fluid is defined as shear stress over shear rate. For non-Newtonian fluids, such as grease, the apparent viscosity changes at different shear rates. The standard method for measuring grease apparent viscosity is defined by ASTM D-1092. Using this method, the apparent viscosity of a non-Newtonian fluid can be measured at different shear rates. However, this method has several drawbacks. The test involves expensive equipment and takes time and effort to run. Further, a separate test must be run for each selected shear rate. Also, the test is not useful at shear rates less than 10 $\sec^{-1}$.

SUMMARY OF THE INVENTION

This invention is directed to a method of estimating an apparent viscosity of a non-Newtonian fluid by using test apparatus. The test apparatus comprises a conduit for receiving a non-Newtonian fluid under pressure, the conduit having an inside diameter D, a length L and a L/D ratio greater than 40, a valve system operable in a first mode to block fluid flow in the conduit to allow fluid to accumulate under pressure in a pressure zone of the conduit and in a second mode to vent the pressure zone of the conduit, and a pressure measuring device for measuring the pressure inside the pressure zone of the conduit. The method comprises a) with the valve system operating in its first mode, supplying fluid under pressure to the conduit until the fluid in said pressure zone reaches a predetermined pressure;

b) operating the valve system in its second mode to vent the pressure zone of the conduit for a predetermined time interval during which there is a transition between non-Newtonian flow and Newtonian flow;

c) using the pressure measuring device, measuring the pressure P in the pressure zone during the transition;

d) calculating a wall shear stress τ of the fluid based on conduit length L, conduit diameter D, and the measured pressure P during the transition; and e) determining an estimated apparent viscosity $\eta_{est}$ of the fluid at a selected shear rate using a first formula $\eta_{est} = \tau/\gamma_s$, where τ is the calculated wall shear stress and $\gamma_s$ is the selected shear rate not based on any measurement of fluid output from the conduit.

In another aspect, a method of this invention further comprises the step of selecting equipment for a pumping system based at least in part on the estimated apparent viscosity $\eta_{est}$.

In another aspect, this invention is directed to a system for estimating an apparent viscosity of a non-Newtonian fluid. The system comprises a conduit for receiving fluid under pressure, the conduit having an inside diameter D, a length L and a L/D ratio greater than 40. A valve system is operable in a first mode to block fluid flow in the conduit to allow fluid to accumulate under pressure in a pressure zone of the conduit and in a second mode to vent the pressure zone of the conduit. A pressure measuring device is provided for measuring the pressure inside the pressure zone of the conduit. The pressure measuring device provides a pressure signal indicative of the pressure inside the pressure zone. A controller selectively operates the valve system in the first and second modes and receives the pressure signal. The controller also provides output information indicative of the viscosity of the fluid based on the conduit length L, conduit diameter D, and a measured pressure P when the valve mechanism is open and the fluid transitions from non-Newtonian flow to Newtonian flow. The viscosity is not based on any measurement of fluid output from the conduit.

Other objects and features will be in part apparent and in part pointed out hereinafter.

BRIEF DESCRIPTION OF THE DRAWINGS

FIG. 1A is a schematic view of a fluid dispensing system;

FIGS. 6-13 are graphs comparing the estimated apparent viscosity of a non-Newtonian fluid determined by a test procedure of this invention and the viscosity of the fluid as determined by a ASTM-D-1092 test method;

Corresponding reference characters indicate corresponding parts throughout the drawings.

DETAILED DESCRIPTION

Figure 1B:
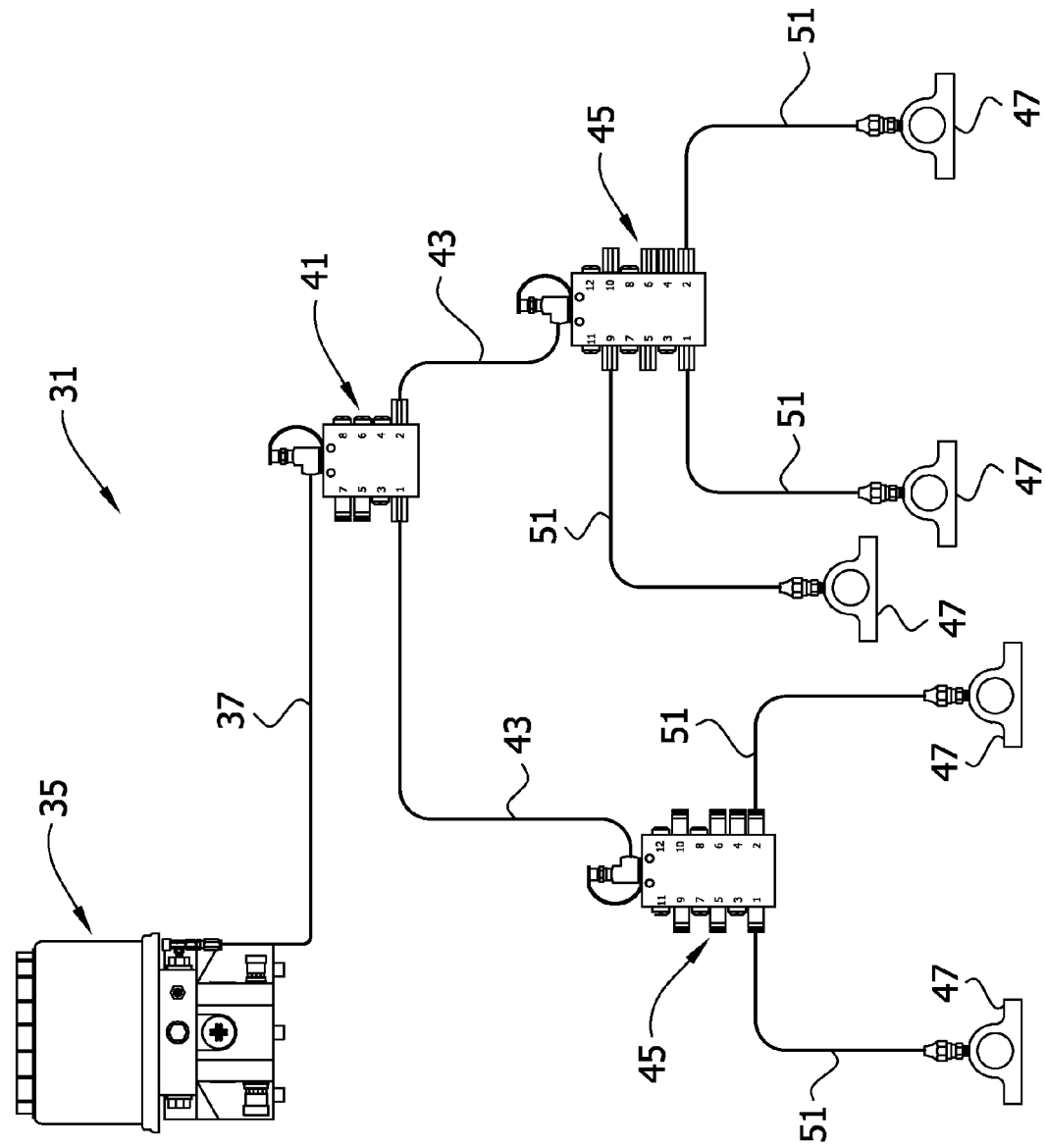
FIG. 1B is a schematic view of a progressive lubrication system.

In general, this invention is useful in the design of non-Newtonian fluid flow systems by providing a method of determining apparent viscosity. The design of a fluid flow system involves the determination of pressure drop in the system. To determine pressure drop, it is necessary to know the apparent viscosity of the fluid because the amount of pressure drop will vary depending on the apparent viscosity of the fluid used in the system. As apparent viscosity increases, the pressure drop inside supply and feed lines will also increase, and greater pump power is required for a given flow rate. The converse is also true. As apparent viscosity decreases, the pressure drop will decrease and less pump power will be needed. The method and apparatus of this invention for estimating apparent viscosity of a non-Newtonian fluid can be applied to many fluid flow systems, especially to those with flow generating shear rates in the range of 1-150 sec$^{-1}$. FIGS. 1A and 1B illustrate two such systems, which are intended to be exemplary only.

FIG. 1A shows a typical fluid dispensing system, generally designated 1. In general, the system comprises a reservoir 5 of lubricating fluid and an air-operated pump 7 for pumping fluid through a supply line 9 attached to a hose reel 11 and from there through a feed line 13 to a dispenser 15. The operation of the system is controlled by controller 17 which operates a solenoid valve 19 to control the supply of pressurized air from a source 21 to the pump and a 3-way vent valve 25 for venting fluid back to the reservoir 5. The fluid power capacity of the pump 7 needs to be properly sized to overcome the pressure drop in both the supply line 9 and the feed line 13. Apparent viscosity is required to calculate the pressure drop over these lines at the required flow rate. Apparent viscosity is also needed to size the tubing or piping when the fluid power capacity of the pump is known.

Similar calculations are necessary to properly size the fluid power capacity of the pump and tubing in a progressive lubrication system, such as the progressive system 31 shown in FIG. 1B. In this system a pump 35 pumps fluid through a primary supply line 37 to a primary distributor valve 41 and then through secondary supply lines 43 to secondary distributor valves 45. Fluid is delivered to points of lubrication 47 (e.g., bearings) via feed lines 51 attached to outlets of the secondary distributor valves 45. The flow rate required in such a system can be calculated based on the rate at which fluid is dispensed from the valves 41 and 45. Apparent viscosity is useful information for proper selection of pump capacity, line size, and the limit of the longest fluid path in this system and other systems having various types of fluid dispensers (e.g., injectors, divider valves, fuel meters, etc.).

Figure 2:
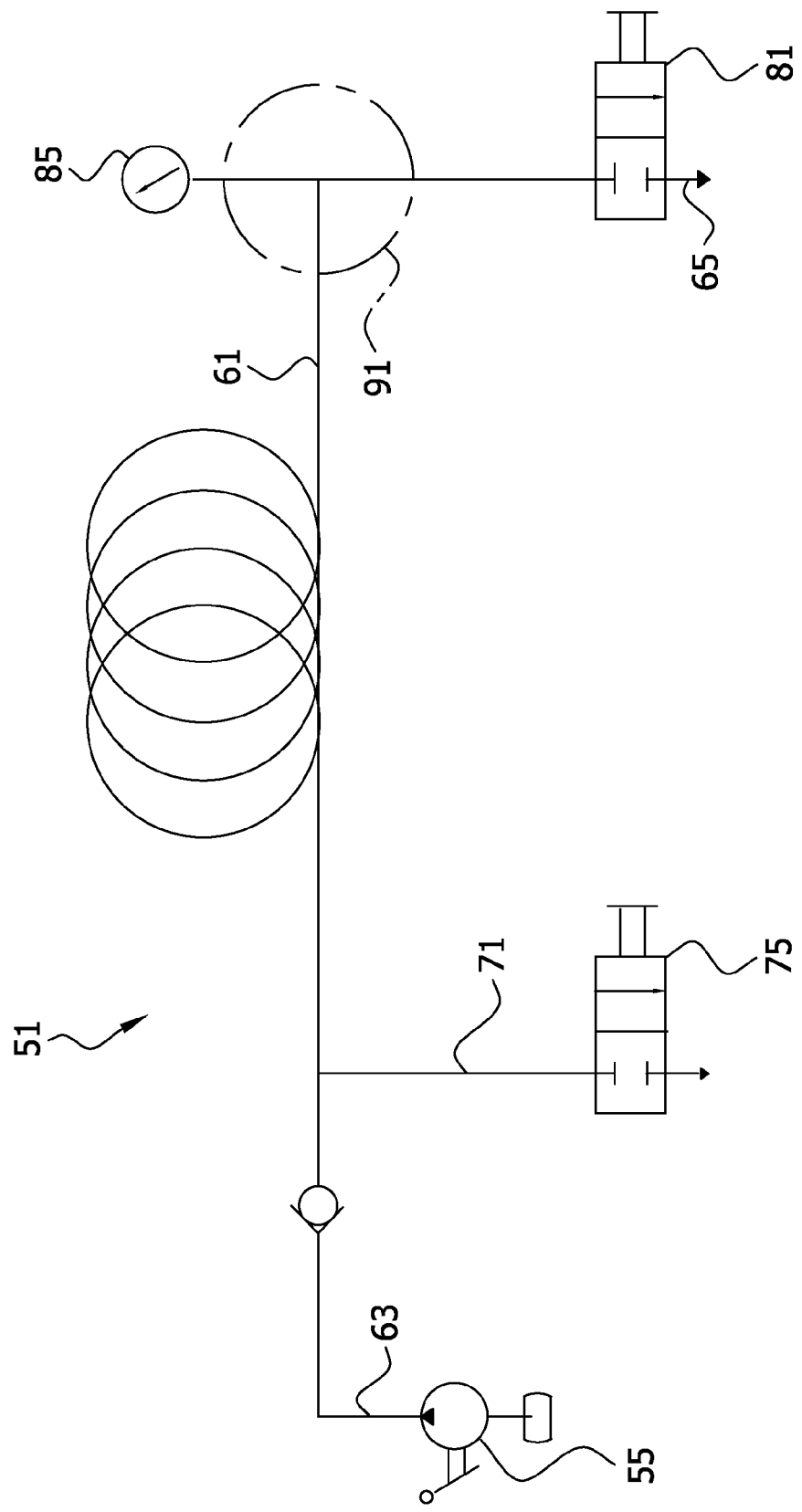
FIG. 2 is a schematic view of a "Ventmeter" tester used to carry out a method of this invention for estimating the apparent viscosity of a non-Newtonian fluid.
Figure 3:
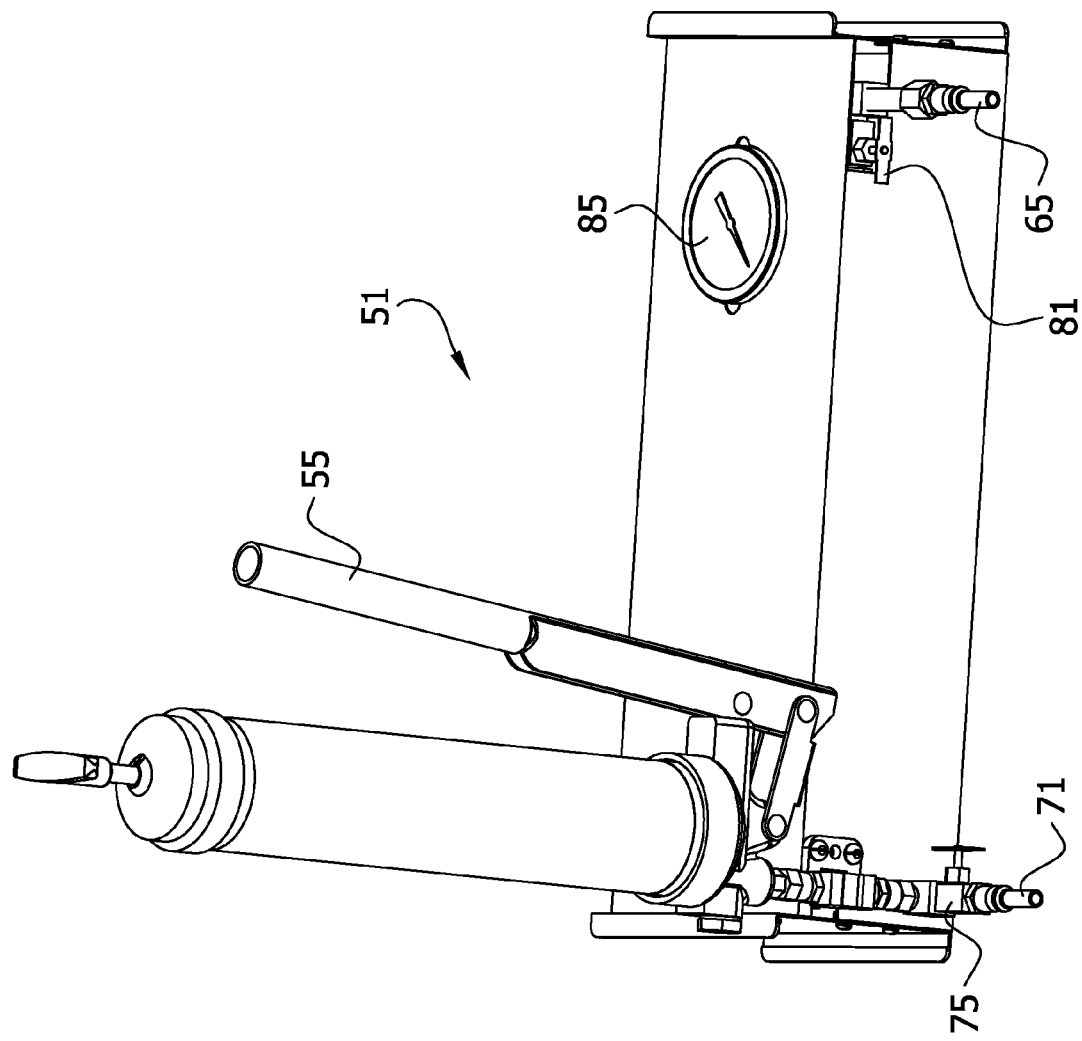
FIG. 3 is a perspective of an exemplary apparatus incorporating the equipment of FIG. 2.

One useful tool that has been used by design engineers is the "Ventmeter" tester, developed years ago by Lincoln Industries of St. Louis, Mo. This tester simulates the conditions and operation of a centralized lubrication system. As shown in FIGS. 2 and 3, the tester 51 is equipped with a pump 55 comprising a manually operated lever-actuated grease gun, a length of conduit comprising a coiled metal tube 61 having an inlet end 63 communicating with the pump and an outlet end 65, a relatively short vent line 71 communicating with the coiled tube 61 downstream from and generally adjacent the pump 55, a valve system comprising a first (venting) valve 75 in the vent line 71, a second valve 81 generally adjacent the outlet end 65 of the coiled tube 61, and a pressure measuring device 85 (e.g., a pressure gauge) upstream from and generally adjacent the second valve 81 for measuring and displaying the pressure in a pressure zone 91 of the coiled tube. This pressure zone 91 is typically the area inside the tube 61 at the location of the pressure measuring device 85.

In one embodiment, the coiled metal tube 61 of the "Ventmeter" has a length of about 25 feet and an inside (flow) diameter of about 0.25 in. The tube may have other lengths and diameters. Desirably, the tube has a length (L) to diameter (D) ratio greater than 40 and even more desirably greater than 500. The vent line 71 has a flow diameter about the same as the flow diameter of the coiled tube 61, and desirably not substantially smaller than that of the coiled tube 61 so that it does not restrict flow from the tube during venting, as will be described.

In one embodiment, the two valves 75, 81 are needle valves movable manually between open and closed positions. In another embodiment, one or both valves are solenoid-operated valves. The first (venting) valve has a flow orifice not substantially smaller in diameter than the flow diameter of the coiled tube, and desirably about the same size or larger than the flow diameter of coiled tube so that the valve does not restrict the venting process, as will be described. Other valve systems are possible, including systems which have only one valve or systems which have more than two valves.

In the embodiment of FIGS. 2 and 3, the pressure measuring device 85 is a pressure gauge. By way of example but not limitation, the pressure gauge may be a mechanical dial gauge with a pressure range of 50-2000 psig.

Figure 4:
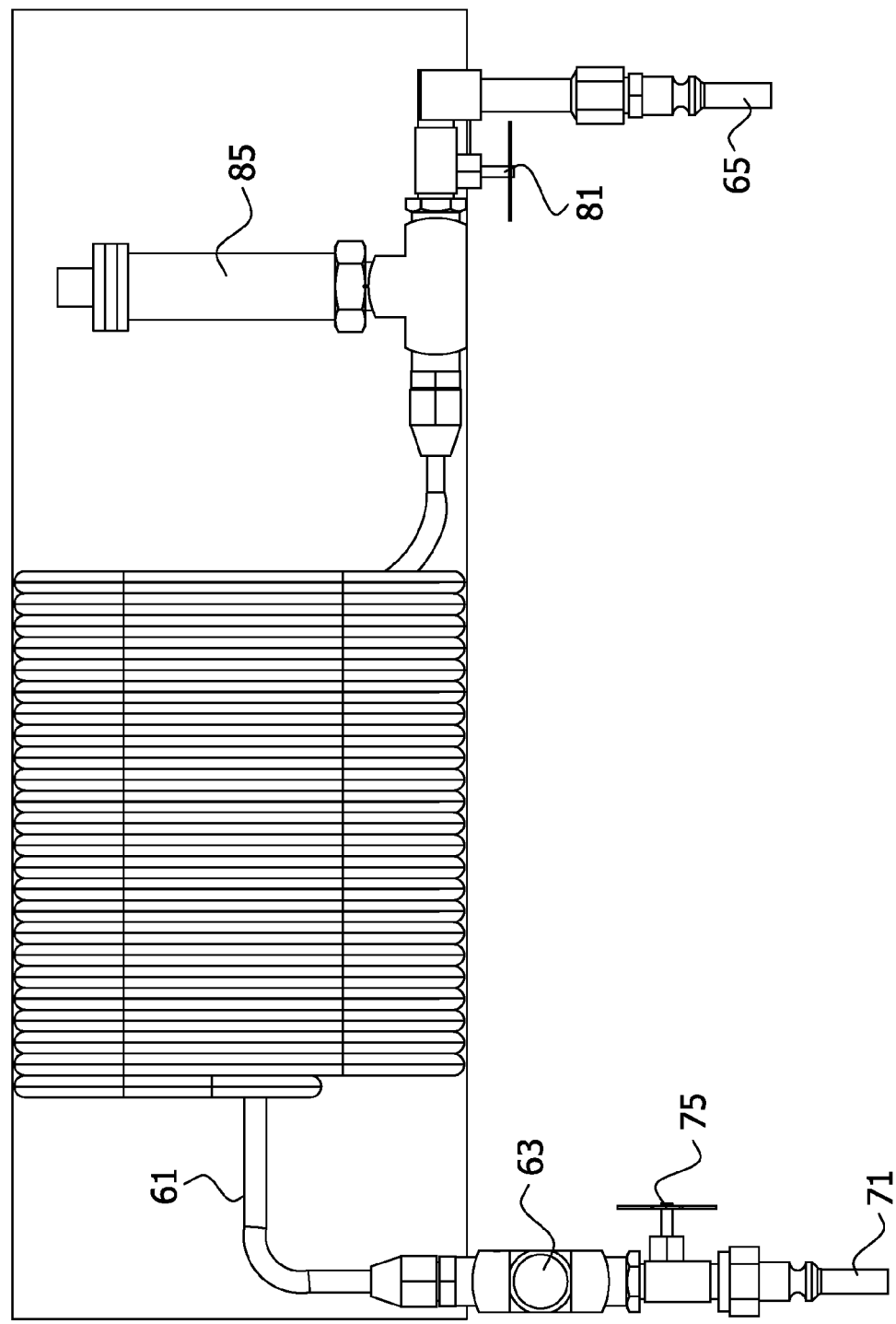
FIG. 4 is view of a second embodiment of a "Ventmeter" tester.

FIG. 4 shows a different "Ventmeter" tester, generally designated 101. The tester 101 is similar to the tester 51 of the previous embodiment, and corresponding parts are designated by the same reference numbers. In the tester 101, the pressure measuring device 85 is a pressure transducer (e.g., a pressure transducer having an analog output).

Prior to the present invention, the "Ventmeter" tester 51, 101 described above was used to estimate apparent viscosity by using the following test procedure. The pump 55 was operated with the first valve 71 closed and the second valve 81 open to prime the system with the lubricating fluid (e.g., grease) to be tested. After the coiled tube 61 was filled with fluid, the second valve 81 was closed to block further flow through the tube, and the pump 55 was operated to supply fluid under pressure to the coiled tube until the fluid in the conduit (i.e., tube 61) reached a predetermined pressure generally in the range of 1500-2200 psig and desirably about 1800 psig as measured by the pressure measuring device 85. The venting valve 75 was then operated (opened) to vent the coiled tube 61 via the vent line 71. During this venting process, the pressure in the tube 61 decreased, at first rapidly and then more slowly. The venting process was allowed to continue for a "venting" interval of time until the rate of pressure decrease was relatively small (e.g., less than about 5 psi/ second over a period of 5 seconds). The pressure in the pressure zone 91 was then measured (using the pressure measuring device 85) and recorded manually. Desirably, the "venting" interval was equal to or greater than 30 seconds for tests conducted at lower temperatures. The weight of fluid vented from the vent line 71 during the "venting" interval was also measured and recorded.

The above information was then used to estimate the apparent viscosity of the lubricating fluid by using a series of calculations, as described below.

First, the wall shear stress of the fluid was calculated using the following formula 1:

$$\tau = PD/4L \qquad \text{(formula 1)},$$

where L is the length of the conduit 61, D is the inside diameter (flow area) of the conduit 61, and P is the pressure in the pressure zone 91 as measured by the pressure measuring device 85 at the end of the "venting" interval.

Second, the approximate shear rate of the fluid was calculated using the following formula 2:

$$\gamma = (32Q)/(\pi D^3) \qquad \text{(formula 2)},$$

where D is the inside diameter (flow area) of the conduit 61, and Q is the flow rate of the fluid vented during the "venting" interval determined by measuring fluid output (weight) over the time of the venting interval.

Third, the apparent viscosity of the fluid was calculated using the following formula 3:

$$\eta_a = \tau/\gamma \qquad \text{(formula 3)}.$$

The present invention represents an improvement over the previous testing methodology because it allows the apparent viscosity of the lubricating fluid to be determined without the need to measure fluid output during the venting process, thereby saving substantial time and effort. The new method can be conducted using the "Ventmeter" tester 51, 101 described above or other test apparatus comprising a conduit (e.g., coiled tube 61) for receiving a non-Newtonian fluid (e.g., grease) under pressure, where the conduit 61 has an inside diameter D, a length L and a L/D ratio greater than 40, a valve system (e.g., valves 75 and 81) operable in a first mode to block fluid flow in the conduit 61 to allow fluid to accumulate under pressure in a pressure zone of the conduit (e.g., pressure zone 91) and in a second mode to vent the pressure zone of the conduit, and a pressure measuring device (e.g., device 85) for measuring the pressure inside the pressure zone of the conduit.

The new method comprises the following steps:

Step (a) with the valve system (e.g., valves 75 and 81) operating in its first mode, supplying fluid under pressure to the conduit (e.g., 61) until the fluid in the pressure zone (e.g., 91) reaches a predetermined pressure;

Step (b) operating the valve system in its second mode to vent the pressure zone of the conduit for a "venting" time interval during which there is a transition between non-Newtonian flow and Newtonian flow;

Step (c) using the pressure measuring device (e.g., 85), measuring the pressure P in the pressure zone (e.g., 91) during the transition;

Step (d) calculating a wall shear stress τ of the fluid based on conduit length L, conduit diameter D, and the measured pressure P during the transition; and Step (e) calculating an estimated apparent viscosity $\eta_{est}$ of the fluid at a selected shear rate using a formula 4:

$$\eta_{est} = \tau/\gamma_s \quad \text{(formula 4)}$$

where τ is the calculated wall shear stress and $\gamma_s$ is the selected shear rate not based on any measurement of fluid output from the conduit.

Figure 5:
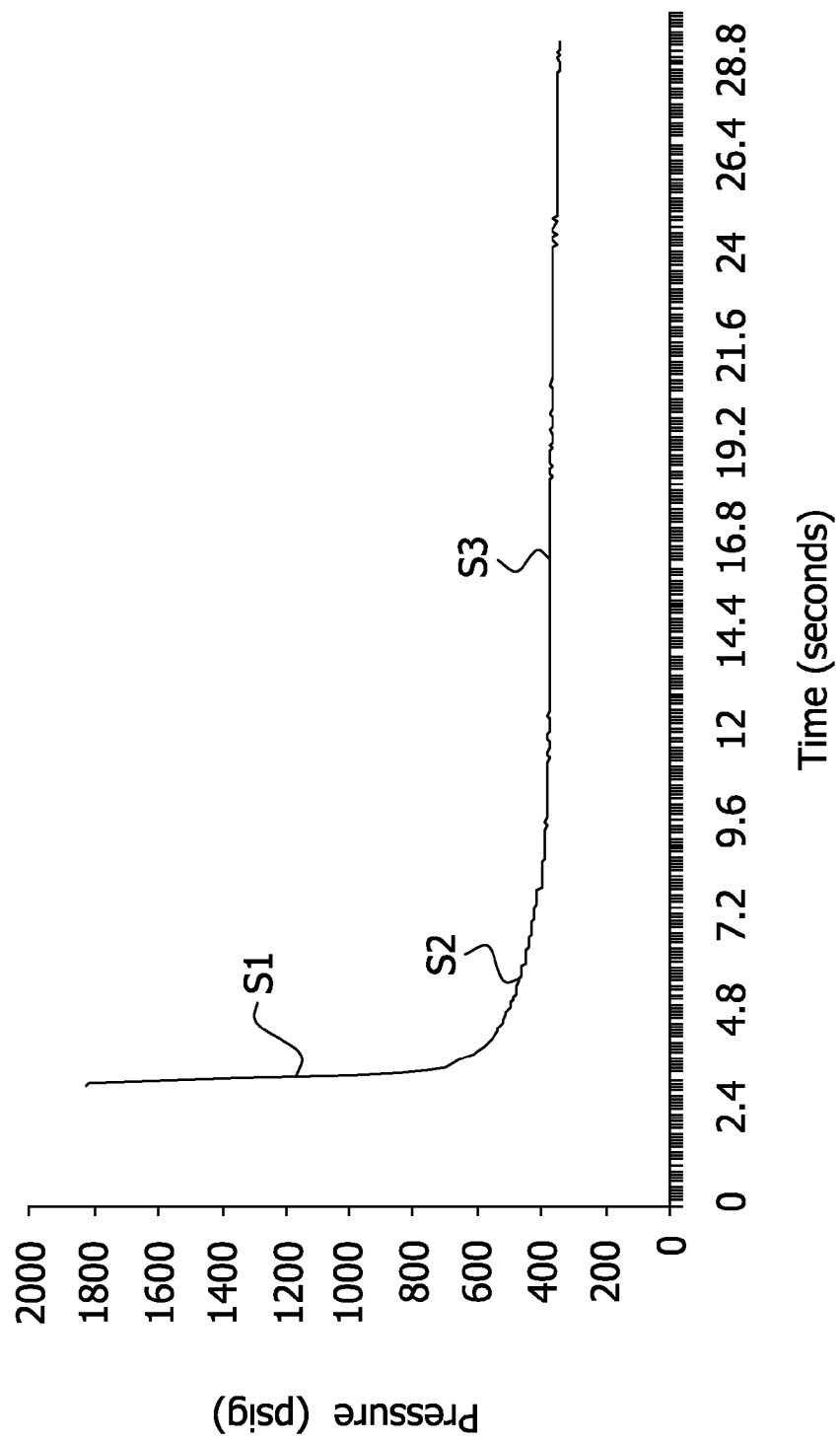
FIG. 5 is a graph showing a pressure curve for a non-Newtonian fluid during a test procedure of this invention.

Using the "Ventmeter" tester (e.g., 51, 101), steps (a) and (b) are carried out in the same manner described above using the previous ("old") test procedure. That is, after the system has been primed and the valves (e.g., 75, 81) moved to their closed positions, lubricating fluid is pumped into the coiled tube (e.g., 61) until the pressure reaches the desired predetermined pressure (e.g., in the range of 1500-2200 psig, and desirably about 1800 psig). The venting valve (e.g., 75) is then opened to vent the coiled tube for a venting time interval (e.g., 30 seconds) during which there is a transition from non-Newtonian flow and Newtonian flow. This transition is best illustrated in the graph of FIG. 5 showing the pressure drop during a "Ventmeter" test. It will be observed from this graph that the pressure curve has three distinct segments. The first segment S1 (from time t=0 seconds to about t=1 second) has a steep relatively constant downward slope indicating a sharp rate of pressure drop (characteristic of non-Newtonian fluid flow). The third segment S3 (from about time t=5 seconds to about t=30 seconds) has a shallow relatively constant downward slope indicating a small rate of pressure drop (characteristic of Newtonian fluid flow). The second segment S2 (from about time t=1 second to about t=5 seconds) has a changing (curvilinear) slope indicating a transition from non-Newtonian fluid flow to Newtonian fluid flow. The specific shape of the curve varies according to such factors as the type of non-Newtonian fluid being tested and the temperature conditions. In general, however, all Non-Newtonian fluids (e.g., greases, ink and adhesives) will exhibit the same type of three-segment curve. Further, for such fluids at room temperature, the transition from non-Newtonian fluid flow to Newtonian fluid flow generally starts at about time t=1 second and generally ends at some time before time t=10 seconds, and typically before about time t=5 seconds.

In step (c) of the test method of the present invention, the pressure in the conduit pressure zone (e.g., 91) is measured at some time during the transition from non-Newtonian to Newtonian fluid flow. In the example of FIG. 5, the pressure is measured (using the pressure measuring device 85) at some time during the interval from about t=1 second to about t=5 seconds (e.g., about time t=2 seconds). Using this single pressure measurement, an estimated apparent viscosity of the fluid can be calculated in steps (d) and (e), as described below.

In step (d) the wall shear stress τ of the fluid is calculated based on conduit length L, conduit diameter D, and the measured pressure P during the transition. In particular, the following formula may be used: τ=PD/4L (formula 1).

In step (e), an estimated (extrapolated) apparent viscosity $\eta_{est}$ of the fluid can be calculated at a selected shear rate by using formula 4:

$$\eta_{est} = \tau/\gamma_s \quad \text{(formula 4)}$$

where τ is the wall shear stress calculated using formula 1 and $\gamma_s$ is the selected shear rate. The selected shear rate is desirably in the range of 1 to 150 sec$^{-1}$. Many fluids (greases, inks, adhesives, etc.) have shear rates in this range under typical dispensing and delivering conditions.

As a result, the estimated apparent viscosity at a selected shear rate can be calculated using just one pressure reading and avoiding the need to determine shear rate which would require measuring the fluid output (weight) over the time of the venting interval. As noted below with regard to FIGS. 6-13, the estimated apparent viscosity compares favorably with the ASTM test results. Thus, the estimated apparent viscosity may be used to size pumps and other components of fluid flow systems. Alternatively and in addition, the estimated apparent viscosity may be used to compare shear stress at various selected shear rates. Alternatively and in addition, as noted below, the estimated apparent viscosity may be used to calculate an adjusted estimated apparent viscosity which more closely approximates the apparent shear stress values as determined by the ASTM test method.

EXAMPLE

The following non-limiting example is provided to further illustrate steps (a) to (e) above. In this example, three tests were conducted, each involving steps (a) to (e). In each test, the "venting" interval was initiated when the pressure in the pressure zone, as measured by the pressure measuring device 85, reached about 1800 psi. During the venting interval, a pressure reading P was taken during the transition S2 (e.g., at about t=2 seconds). The tests results are tabulated below in Table 1.

TABLE 1

| | Test | | |
|---|---|---|---|
| | 1 | 2 | 3 |
| P (psi) | 496.9 | 535.9 | 514.5 |

Using the information in Table 1, the shear stress was calculated using formula (1) τ=P*D/(4L), where D=0.19 in. (corresponding to the inside (flow) diameter of the coiled tube 19) and L=300 in. (corresponding to the length of the tube). This calculation resulted in the information in Table 2 below.

TABLE 2

| | Test | | |
|---|---|---|---|
| | 1 | 2 | 3 |
| P (psi) | 496.9 | 535.9 | 514.5 |
| τ = P * D/(4L) (lbs/in$^2$) | 0.07868 | 0.08485 | 0.08146 |
| τ(mil-Pascal) | 542451 | 585026 | 561664 |

Using the information in Table 2, the estimated apparent viscosity was calculated using formula (4) $\eta_{est}=\tau/\gamma_s$ (formula 4) at a selected shear rate of 67 sec$^{-1}$, yielding the results in Table 3 below.

TABLE 3

| | Test | | |
|---|---|---|---|
| | 1 | 2 | 3 |
| P (psi) | 496.9 | 535.9 | 514.5 |
| τ (mil-Pascal) | 542451 | 585026 | 561664 |
| $\eta_{est}=\tau/67$ (cP) | 8096.3 | 8731.7 | 8383.0 |

Optionally, the method of the present invention may also include a step (f) which calculates an "adjusted" estimated apparent viscosity having a value which correlates (compares to) the results of the ASTM D-1092 test method. In this step (f), the adjusted estimated apparent viscosity is calculated using the following formula 5:

$$\eta_{adj}=\eta_{est}(\gamma_s/\gamma_{ref})^n \quad \text{(formula 5)},$$

where $\eta_{est}$ is the estimated apparent viscosity calculated using formula 4, $\gamma_s$ is the selected shear rate (e.g., in the range of 1-150 sec$^{-1}$), $\gamma_{ref}$ is a reference shear rate (to be explained later), and "n" is relatively stable number for a type of fluid at certain temperature in the selected shear rate range of 1-150 sec$^{-1}$ (to be explained later).

Table 4 below represents the adjusted estimated apparent viscosities calculated using formula 5 and the information in Table 3. Three iterations of the test were run (i.e., Tests 1, 2, and 3) and two calculations were made, the first based on the results of Test 1 and the second on the results of Test 2. The results of Test 3 were not used. In the first calculation, the following numbers were used: $\eta_{est}$=8096.3 cP; $\gamma_{ref}$=20 sec$^{-1}$; "n"=0.36; and a selected shear rate of 67 (cP). In the second calculation, the following numbers were used: $\eta_{est}$=8731.7 cP; $\gamma_{ref}$=30 sec$^{-1}$; "n"=0.36; and a selected shear rate $\gamma_s$ of 67 sec$^{-1}$.

TABLE 4

| Test | 1 | 2 | 3 |
|---|---|---|---|
| P (psi) | 496.9 | 535.9 | 514.5 |
| τ(mil-Pascal) | 542451 | 585026 | |
| $\eta_{est}=\tau/67$ (cP) | 8096.3 | 8731.7 | |
| $\eta_{adj}=\eta_{est}(\gamma_s/\gamma_{ref=20})^n$ | | = 8731.1*(67/30)$^{.36}$ = 11660.7 | |
| $\eta_{adj}=\eta_{est}(\gamma_s/\gamma_{ref=30})^n$ | = 8096.3*(67/20)$^{.36}$ = 12511.3 | | |

It will be observed from Table 4 that the adjusted estimated apparent viscosity at a shear rate of 67 sec$^{-1}$ for Test 1 and Test 2 are 12511.3 cP and 11660.7 cP, respectively or, in other words, within a range of 11660.7-12511.3 cP. Table 5 below shows the apparent viscosities determined using the ASTM D-1092 test procedure.

TABLE 5

| Shear Rate | Apparent Viscosity |
|---|---|
| 17.0 | 35397.0 |
| 23.0 | 27143.0 |
| 33.0 | 20992.0 |
| 50.0 | 15713.0 |
| 67.0 | 12488.0 |

Thus, at a shear rate of 67.0 sec$^{-1}$, it will be observed that the adjusted estimated apparent viscosity determined by the test method of the present invention (i.e., 11660.7-12511.3 cP) compares favorably to the value obtained using the ASTM D-1092 test procedure.

In the above tests, steps (a)-(e) were repeated three times to determine three estimated apparent viscosities, and the largest and smallest of the three estimated apparent viscosities were used to calculate the corresponding adjusted estimated apparent viscosities. However, it will be understood that the number of tests conducted can vary from one to two or more. In one example, at least two tests are conducted to determine at least two estimated apparent viscosities $\eta_{esthigh}$ and $\eta_{estlow}$, where $\eta_{esthigh}$ is the greater of the two values. These values are then used to calculate an adjusted estimated apparent viscosity $\eta_{adj}$ using formula 5, and the results are recorded.

Explanation of Adjustment Step (F)

As noted above, the formula used to calculate the adjusted estimated apparent viscosity of a non-Newtonian fluid is $\eta_{adj}=\eta_{est}(\gamma_s/\gamma_{ref})^n$ (formula 5). The manner by which this formula was derived is explained below.

Figure 5A:
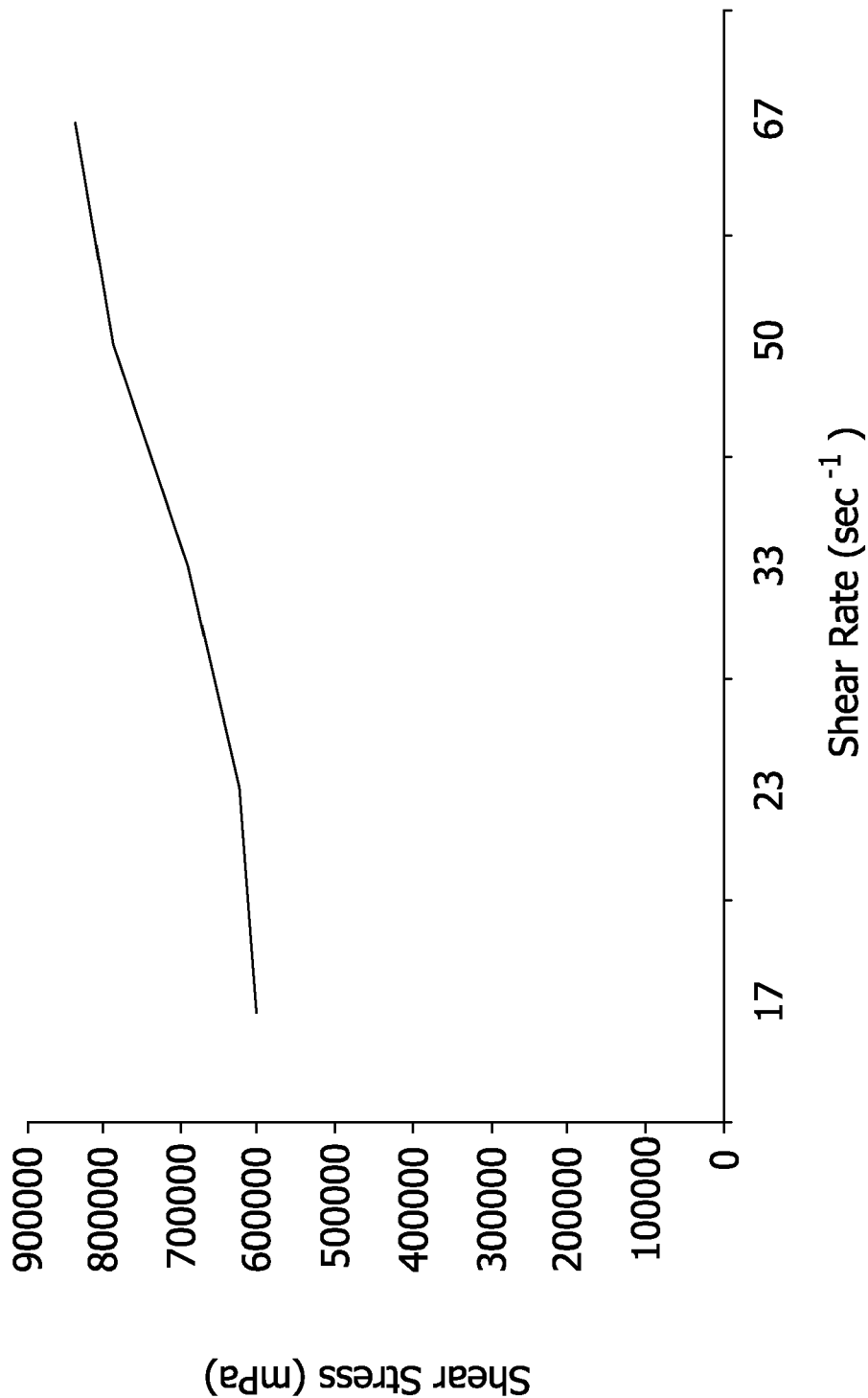
FIG. 5A is a graph showing shear stress v. shear rate for a non-Newtonian fluid.
Figure 7:
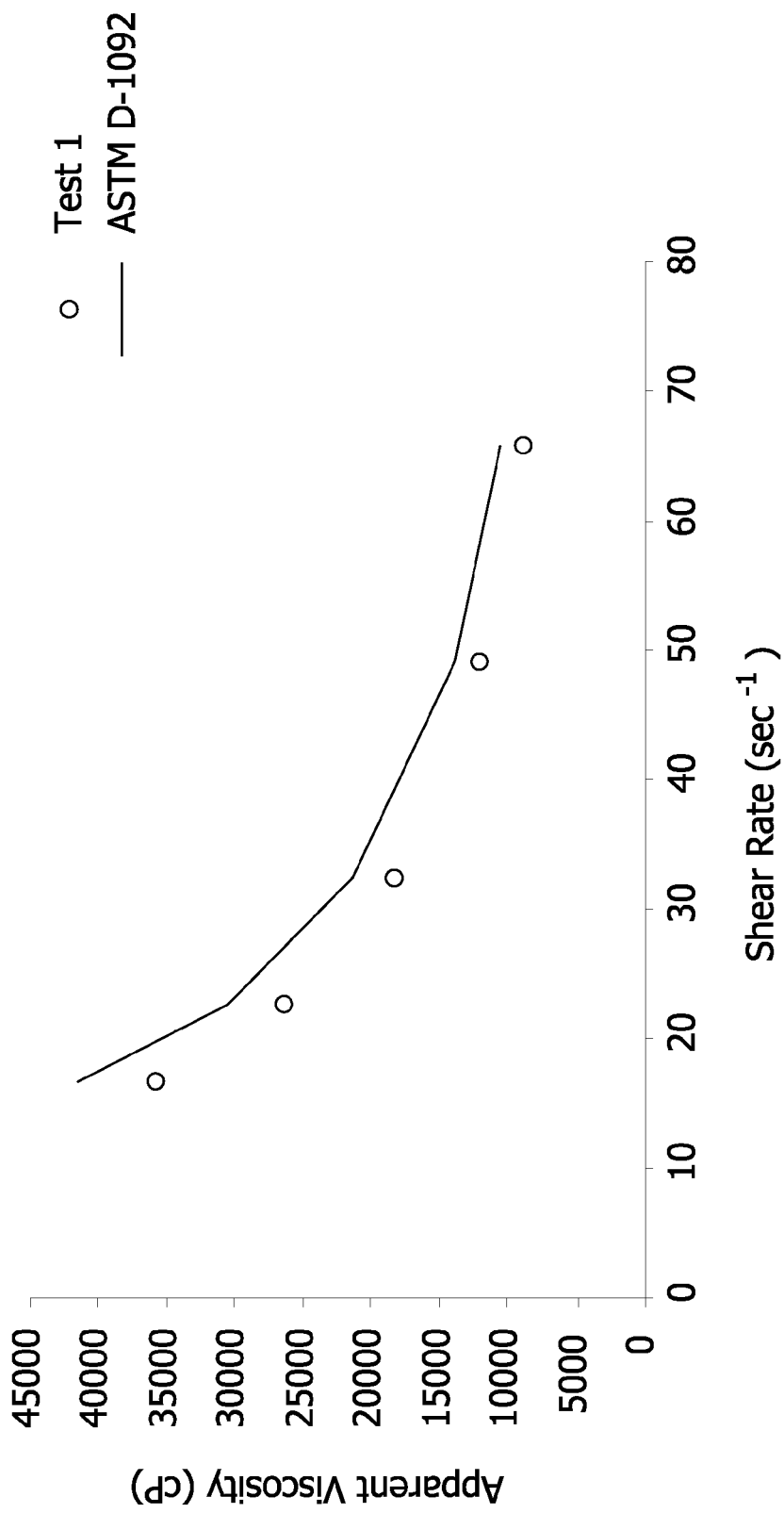
Figure 8:
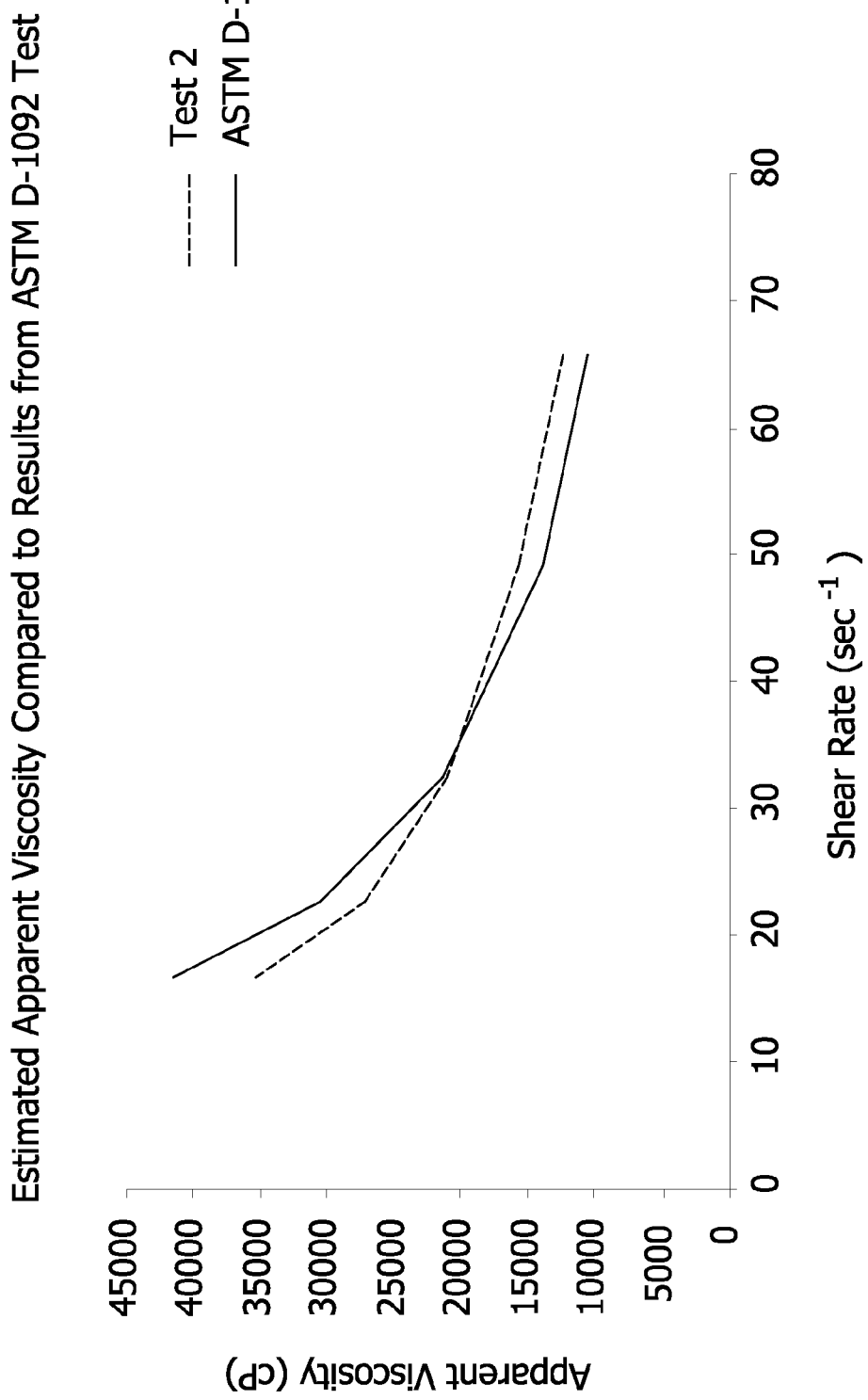
Figure 9:
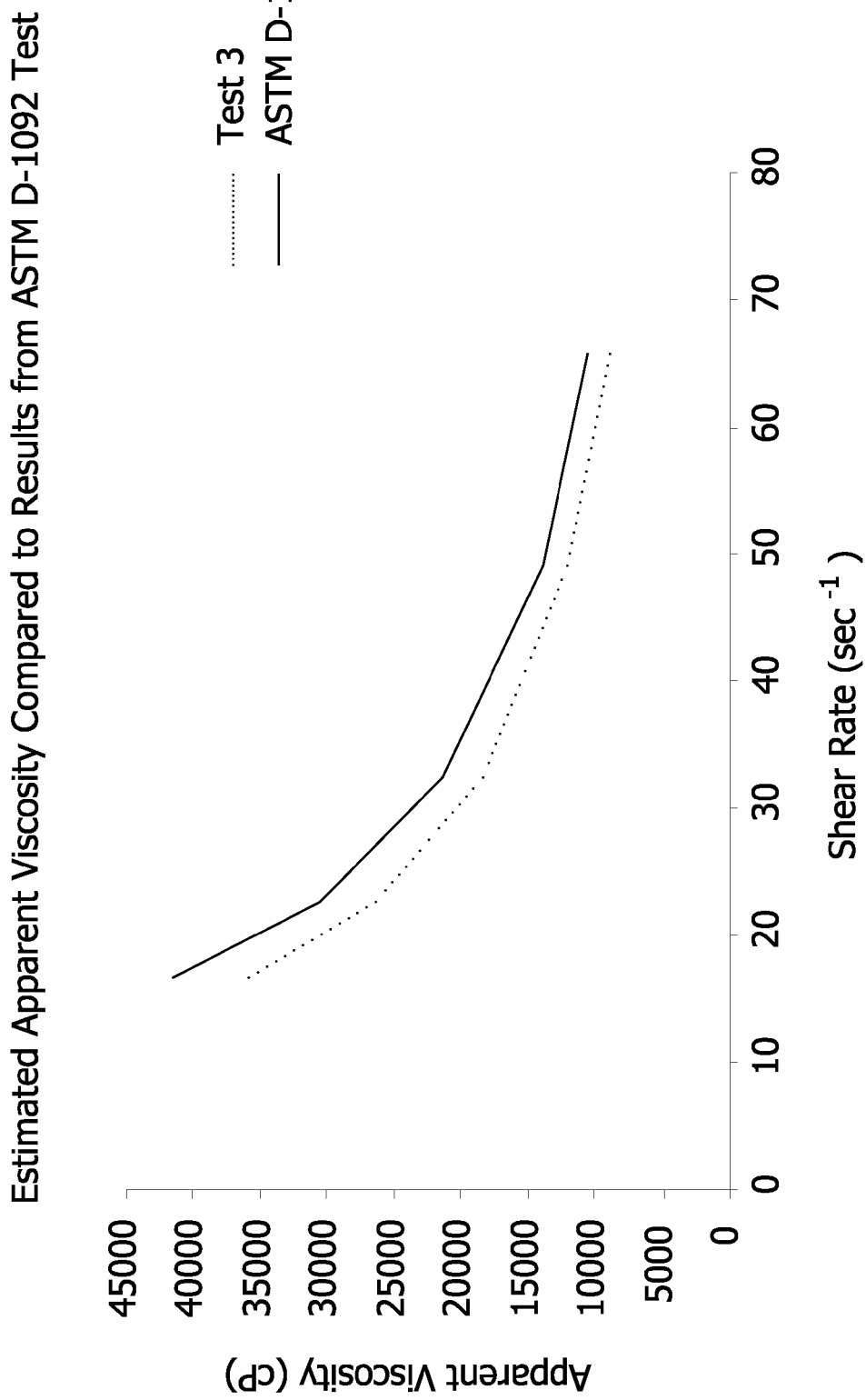
Figure 10:
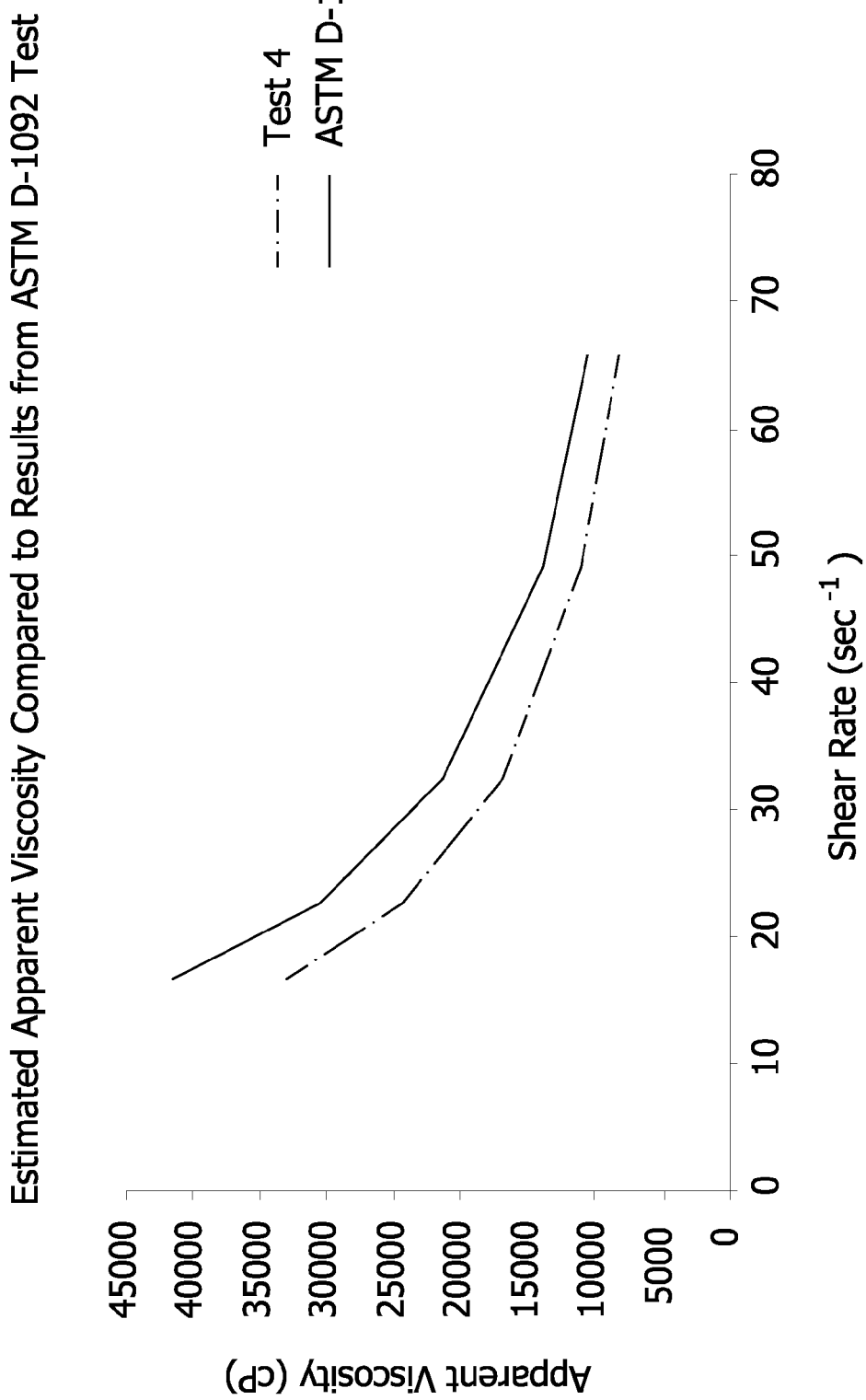
Figure 11:
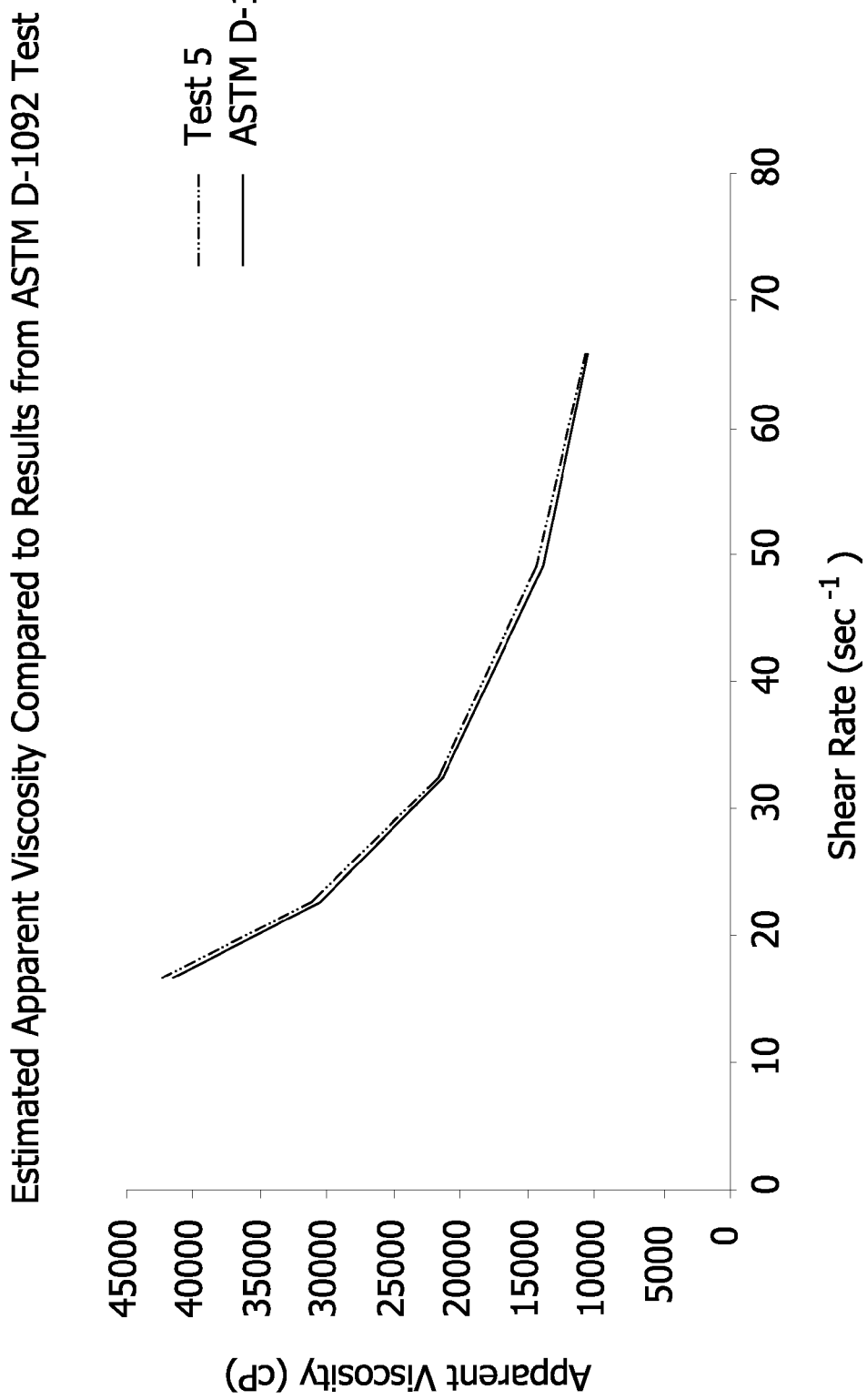
Figure 12:
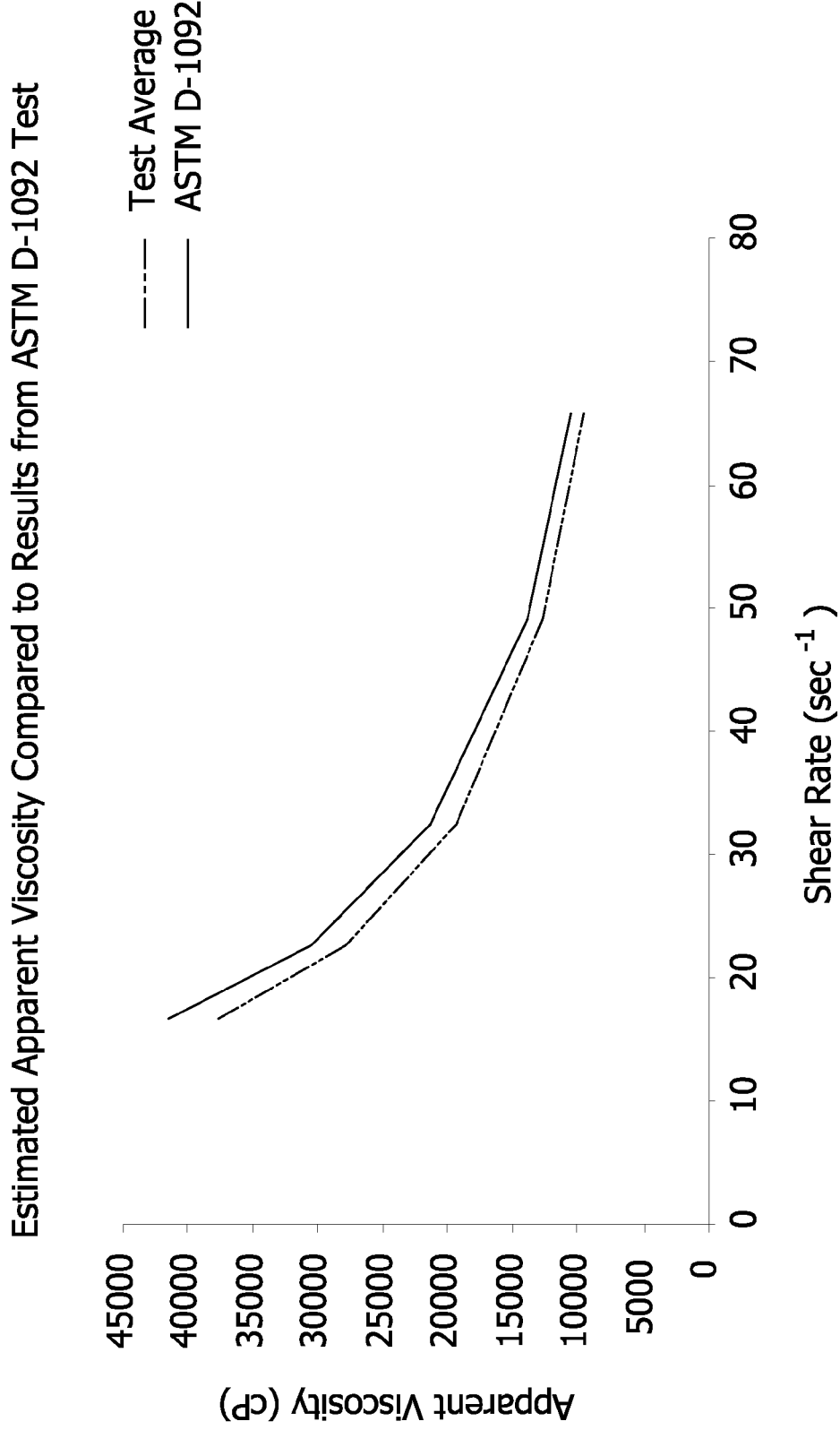
Figure 13:
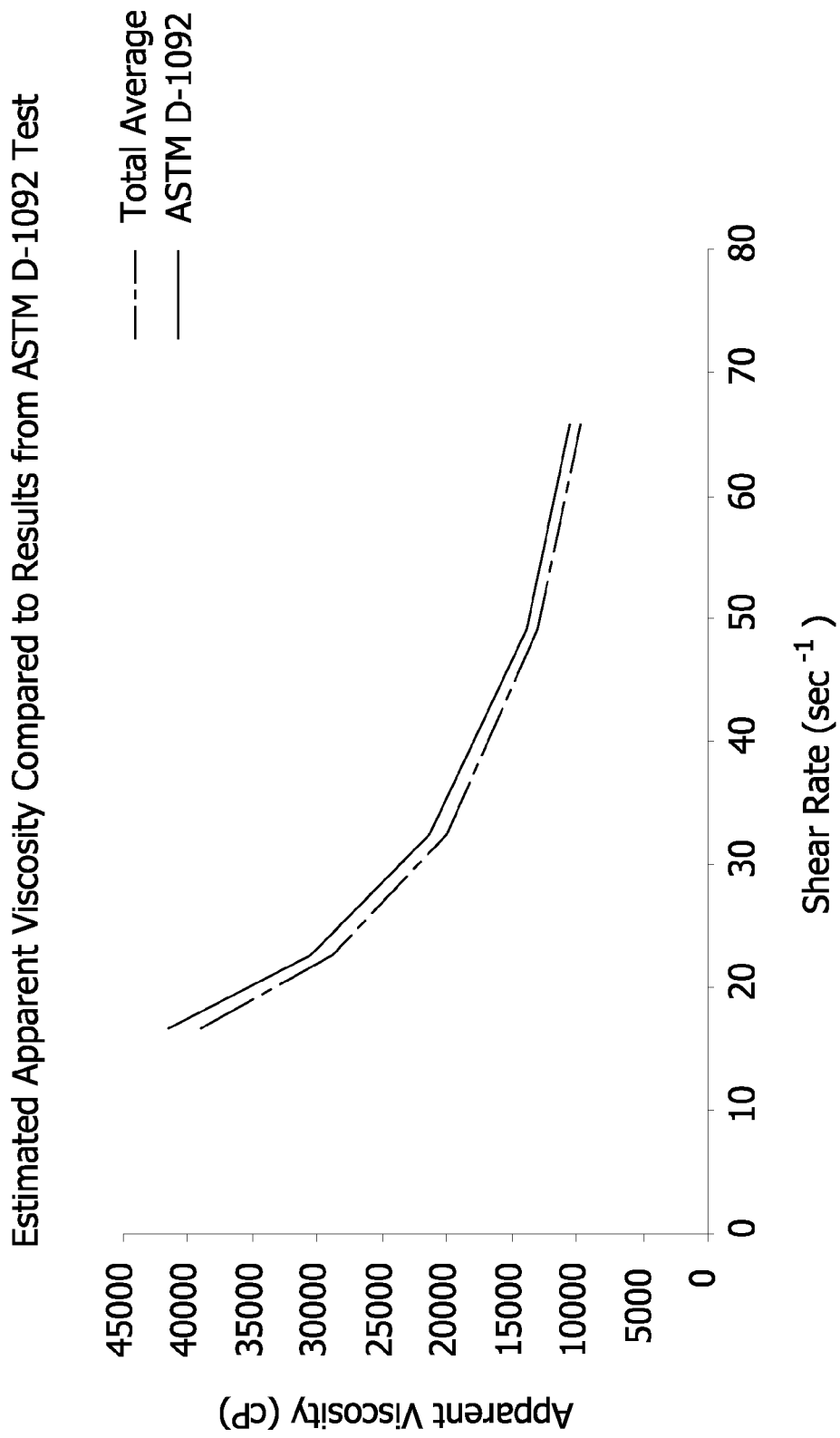

FIG. 5A is a graph of shear stress vs. shear rate in the range of 17-67 sec$^{-1}$ based on tests conducted on a non-Newtonian shear-thinning fluid (e.g., a lubricating fluid such as grease) using the test procedure of ASTM D-1092. It will be observed from this graph that the shear stress over shear rates of this type of fluid exhibits a power-law relation. Therefore, the shear stress τ can be defined according to the power-law relation as a function of the shear rate γ to the power "n":

$$\tau=K^*\gamma^n \quad \text{(formula 6)},$$

where K is an unknown constant. Thus, the shear stress at two different times t1 and t2 (e.g., at a first time during the transition segment S2 of the "venting" interval and at a second time during the Newtonian segment S2 of the "venting" interval) would be:

$$\tau_1=K^*(\gamma_1)^n$$

$$\tau_2=K^*(\gamma_2)^n$$

or $$\tau_1/\tau_2=(\gamma_1/\gamma_2)^n \quad \text{(formula 7)}.$$

Figure 14:
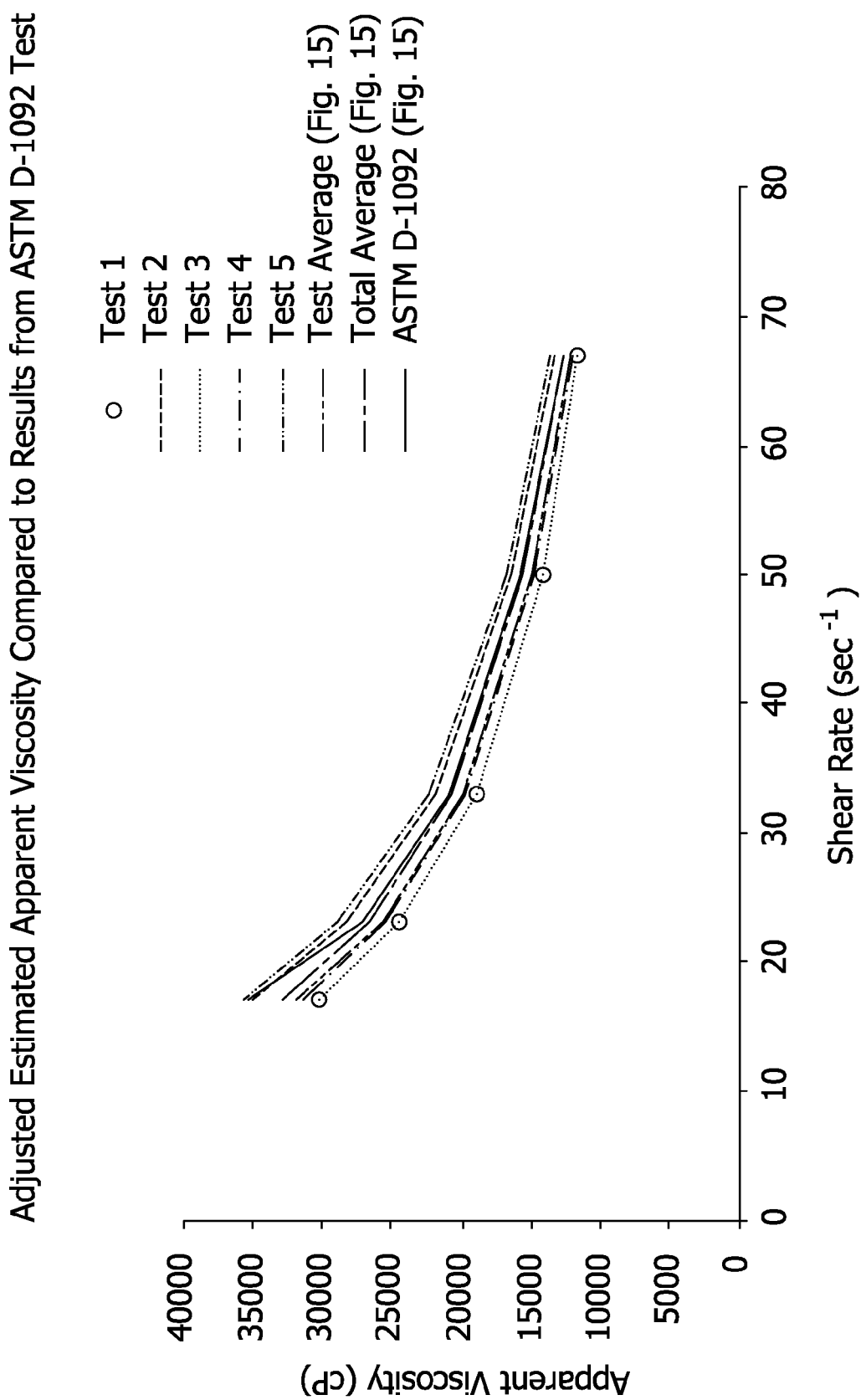
FIG. 14 is a graph comparing adjusted estimated apparent viscosity of a non-Newtonian fluid determined by a test procedure of this invention and the viscosity of the fluid as determined by an ASTM-D-1092 test method.
Figure 15:
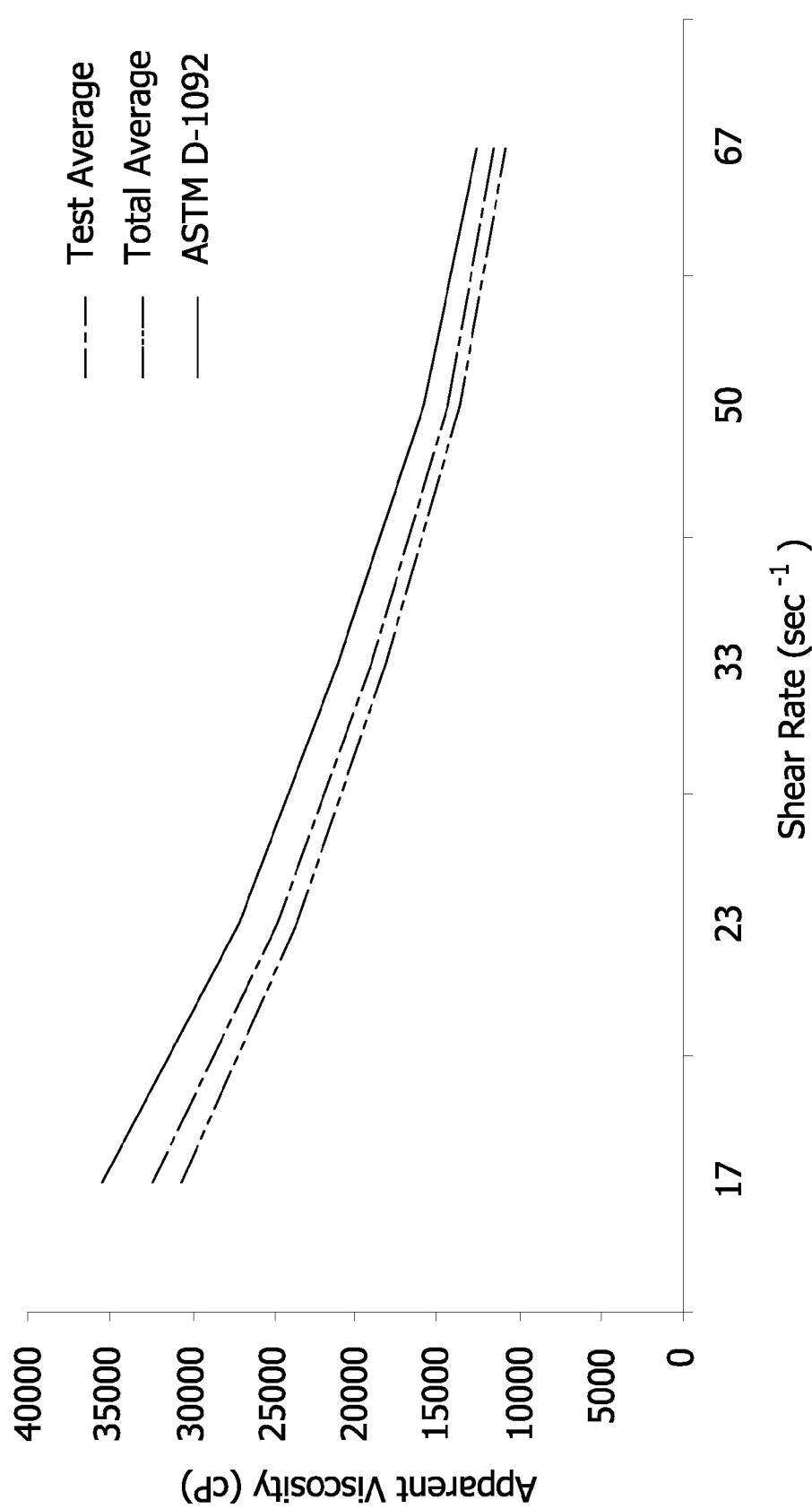
FIG. 15 is a graph comparing test results using the procedure of this invention and results obtained using the procedure of ASTM D-1092.

As noted below with regard to FIGS. 6-13, for shear rates in the approximate range of 20 to 30 sec$^{-1}$, the estimated apparent viscosity corresponds to the apparent viscosity as determined by the ASTM D-1092 test method, or $\eta_{est}=\eta_a$. Within this corresponding range, let us designate a reference shear stress $\tau_{ref}$ and a reference shear rate $\gamma_{ref}$. Substituting these designated references into formula 7 yields:

$$\tau_1/\tau_{ref} = (\gamma_1/\gamma_{ref})^n$$

or $$\tau_1 = \tau_{ref}(\gamma_s/\gamma_{ref})^n \quad \text{(formula 8)},$$

at a selected shear rate $\gamma_s$. From formula 4, we have $\eta = \tau/\gamma_s$, so that substituting formula 8 into formula 4 yields $$\eta_{adj} = \tau_1/\gamma_1 = (\tau_{ref}/\gamma_1)(\gamma_1/\gamma_{ref})^n \quad \text{(formula 9)},$$

at a selected shear rate $\gamma_s$. But $(\tau_{ref}/\gamma_s) = \eta_a = \eta_{est}$ in the approximate range of 20 to 30 sec$^{-1}$, so formula 9 becomes $$\eta_{adj} = \eta_{est}(\gamma_s/\gamma_{ref})^n \quad \text{(formula 5)},$$

for a selected shear rate $\gamma_a$. FIGS. 14 and 15 confirm formula 5.

Explanation of the Value of "n"

The value of "n" can be approximated because it is substantially the same for shear rates in the range of 1 to 150 sec−1. The reason for this is that, as noted above in regard to FIG. 5A, the shear stress over shear rates of non-Newtonian fluids exhibit a power-law relation.

It will be observed from formula 1 that the shear stresses $\tau_1$ and $\tau_2$ are directly proportional to pressure readings P1 and P2 taken at times t1 and t2, respectively, or:

$$\tau_1/\tau_2 = P1/P2$$

or from formula 7

$$P1/P2 = (\gamma_1/\gamma_2)^n \quad \text{(formula 10)}$$

If we consider pressure P1 to be a pressure PS2 measured during the transition segment S2 of the "venting" interval (e.g., at t=2 seconds), and if we consider pressure P2 to be a pressure PS3 as measured during the Newtonian flow segment S3 of the "venting" interval (e.g., at t=30 seconds), then, formula 10 becomes $$PS2/PS3 = (\gamma_{S2}/\gamma_{S3})^n \quad \text{(formula 11)}$$

(The pressure PS3 measured during the non-Newtonian flow segment S3 of FIG. 5 may also be referred to as "$P_{end}$" since it is the last of the three segments of the curve.)

Therefore, taking the natural log of formula 11 yields the following:

$$\ln(PS2/PS3) = n \cdot \ln(\gamma_{S2}/\gamma_{S3})$$

In tests conducted on common lubricating fluids (e.g., greases) using the previous "Ventmeter" test procedure and the ASTM test method, it has been determined that $(\gamma_{S2}/\gamma_{S3})$ is about 3, so that $$n = \ln(PS2/PS3)/\ln 3 \quad \text{(formula 12)}.$$

Using the "Ventmeter" tester 101, three tests were conducted on a lubricating fluid under the same ambient conditions. The initial pressures at the start of the intervals were measured (using device 85) to be 1801 psig, 1787.9 psig, and 1821.1 psig. Pressure readings PS2 and PS3 were taken at times t=about 2 seconds and t=about 30 seconds, respectively, yielding the results in Table 6 below.

TABLE 6

|  | 1 | 2 | 3 | Average |
|---|---|---|---|---|
| Pressure at start of venting interval (psig) | 1801.6 | 1787.9 | 1821.1 |  |
| PS2 at t = 2 sec (psig) | 496.9 | 535.9 | 514.5 | 515.7667 |
| PS3 at t = 30 sec (psig) | 350.4 | 342.6 | 344.5 | 345.8333 |
| "n" (ln(PS2/PS3)/ln3) | 0.32 | 0.41 | 0.37 | 0.36 |

Thus, based on this series of tests, "n" is about 0.36, which closely corresponds to the 0.3 value if "n" calculated using the ASTM data.

In using formula 5 to determine adjusted estimated apparent viscosity, the value of "n" can be determined in different ways. A first way is to assume that it is a particular number which has been determined to be reasonably accurate for the type of non-Newtonian fluid being tested within a specific shear range, such as 0.3 and 0.4 for grease at 72° F. and 32° F., respectively, for shear rates in the range of 1-150 sec$^{-1}$. Alternatively, the value may be calculated as outlined above using pressure measurements PS2 and PS3, where PS2 is a measured pressure in the transition segment S2 of the "venting" interval and PS3 is a measured pressure in the third segment S2 of the "venting" interval. Further, this calculated value may be based on one test or multiple tests using an average of pressure readings PS2 and an average of pressure readings PS3.

Explanation of Correspondence between Adjusted and Apparent Viscosity for Shear Rates in the Approximate Range of 20 to 30 sec$^{-1}$ Table 8 shows the estimated apparent viscosities ($\eta_{est}$) of fluids tested using the test method of this invention, the "Ventmeter" tester 101, and formula 4. The tests were conducted on shear thinning non-Newtonian fluids at shear rates ranging from 1 to 67 sec$^{-1}$. Table 8 also shows the corresponding apparent viscosities determined using the ASTM D-1092 test method at shear rates of 17, 23, 33, 50 and 67 sec$^{-1}$.

TABLE 8

| Shear Rate (sec$^{-1}$) | Test 1 | Test 2 | Test 3 | Test 4 | Test 5 | Test Average | Total Average | ASTM D-1092 |
|---|---|---|---|---|---|---|---|---|
| 1 | 609152 | 704127 | 609152 | 560027 | 717227 | 639937 | 661897 | Data not available |
| 2 | 304576 | 352064 | 304576 | 280013 | 358614 | 319968 | 330948 |  |
| 3 | 203051 | 234709 | 203051 | 186676 | 239076 | 213312 | 220632 |  |
| 5 | 121830 | 140825 | 121830 | 112005 | 143445 | 127987 | 132379 |  |
| 10 | 60915 | 70413 | 60915 | 56003 | 71723 | 63994 | 66190 |  |
| 17 | 35832 | 41419 | 35832 | 32943 | 42190 | 37643 | 38935 | 35397 |
| 23 | 26485 | 30614 | 26485 | 24349 | 31184 | 27823 | 28778 | 27143 |
| 33 | 18459 | 21337 | 18459 | 16971 | 21734 | 19392 | 20057 | 20992 |
| 50 | 12183 | 14083 | 12183 | 11201 | 14345 | 12799 | 13238 | 15713 |
| 67 | 9092 | 10509 | 9092 | 8359 | 10705 | 9551 | 9879 | 12488 |

FIGS. 6-13 are graphs of the data of Table 8 and show how the apparent viscosity curve as determined by the ASTM D-1092 test procedure compares with the "estimated" apparent viscosity curves as determined by the test procedures of this invention, for shear rates in the range of 17~67 sec$^{-1}$. The graphs show that four out of seven "estimated" curves cross over the ASTM D-1092 curve at shear rates of 20~30 sec$^{-1}$. It is also noticed that the "estimated" apparent viscosities are higher at lower shear rates and lower at higher shear rates than the corresponding ASTM D-1092 viscosity. This is because the estimation is made with shear stress at one single shear rate.

Table 9 shows "adjusted" estimated apparent viscosities ($\eta_{adj}$) based on the information in Table 8 and using the power-law relationship incorporated in formula 5, where "n"=0.3, the reference shear rate $\gamma_{ref}$=20 (sec$^{-1}$) for Test 4 and $\gamma_{ref}$=30 (sec$^{-1}$) for Tests 1-3 and 5. Table 9 also shows the corresponding apparent viscosities determined using the ASTM D-1092 test method at shear rates of 17, 23, 33, 50 and 67 sec$^{-1}$.

TABLE 9

| Shear Rate (sec$^{-1}$) | Test 1 | Test 2 | Test 3 | Test 4 | Test 5 | Test Average | Total Average | ASTM D-1092 |
|---|---|---|---|---|---|---|---|---|
| 1 | 219578 | 253813 | 219578 | 227982 | 258536 | 230675 | 238591 | Data |
| 2 | 135166 | 156241 | 135166 | 140339 | 159147 | 141997 | 146870 | not |
| 3 | 101766 | 117633 | 101766 | 105661 | 119822 | 106909 | 110578 | available |
| 5 | 71172 | 82269 | 71172 | 73896 | 83799 | 74769 | 77335 | |
| 10 | 43812 | 50642 | 43812 | 45488 | 51585 | 46026 | 47605 | |
| 17 | 30219 | 34930 | 30219 | 31375 | 35580 | 31746 | 32835 | 35397 |
| 23 | 24456 | 28269 | 24456 | 25392 | 28796 | 25692 | 26573 | 27143 |
| 33 | 18995 | 21956 | 18995 | 19721 | 22365 | 19955 | 20639 | 20992 |
| 50 | 14201 | 16415 | 14201 | 14744 | 16720 | 14918 | 15430 | 15713 |
| 67 | 11570 | 13374 | 11570 | 12013 | 13623 | 12155 | 12572 | 12488 |

Figure 16:
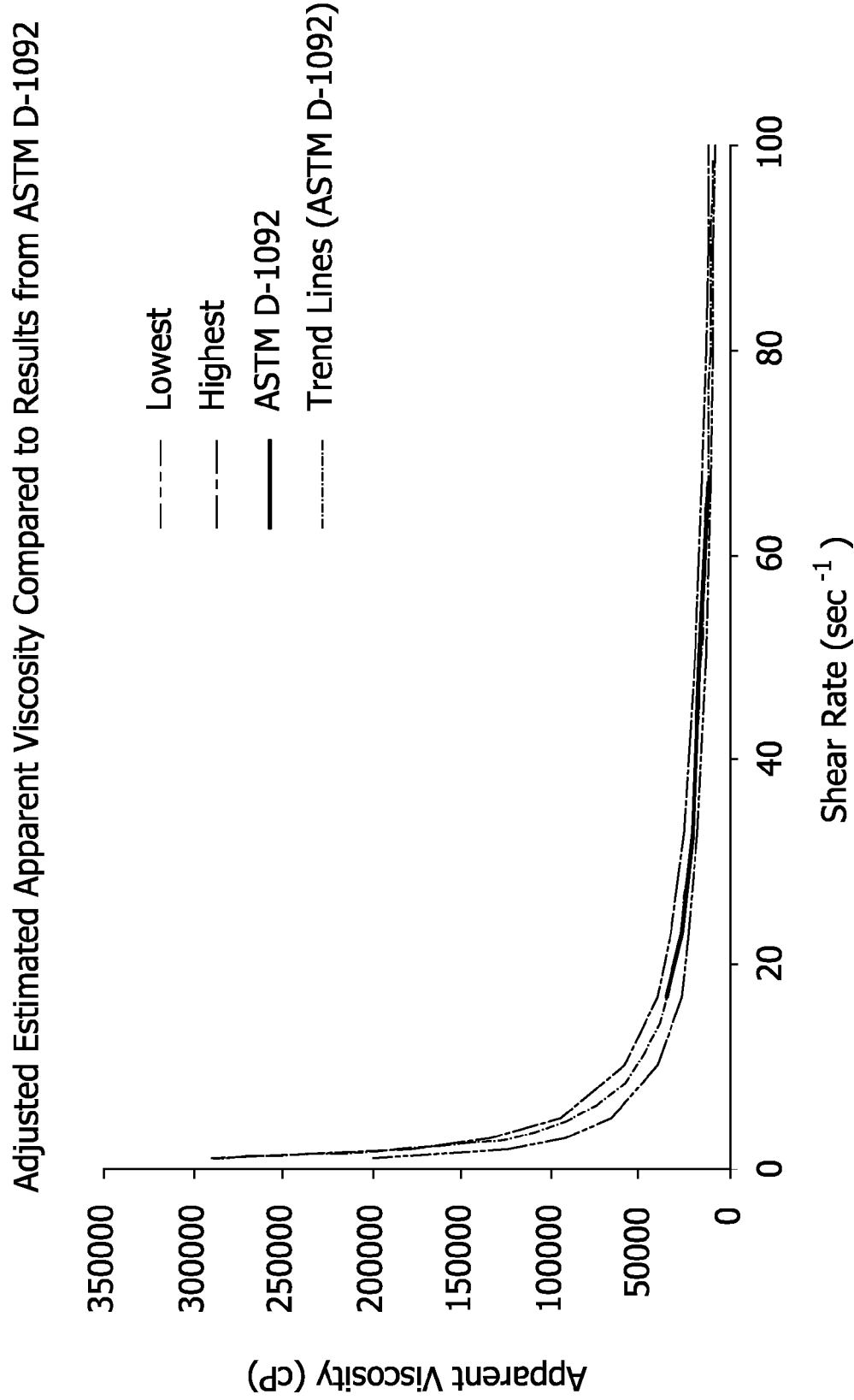
FIG. 16 is a graph comparing adjusted estimated apparent viscosities of a Non-Newtonian fluid determined by a test procedure of this invention with actual and extrapolated test results based on the ASTM D-1092 method.

Table 10 shows the percentage differences between the "adjusted" estimated apparent viscosities in Table 9 and the corresponding viscosities determined by the ASTM D-1092 test. The largest percentage difference is less than 15%. FIGS. 15 and 16 illustrate graphs comparing the adjusted estimated apparent viscosities against viscosities from the ASTM D-1092 test. FIGS. 7-11 illustrate a comparison for each test and FIGS. 12 and 13 a comparison of averages.

TABLE 10

| Shear Rate (sec$^{-1}$) | Test 1 | Test 2 | Test 3 | Test 4 | Test 5 | Test Average | Total Average |
|---|---|---|---|---|---|---|---|
| 17 | −14.6% | −1.3% | −14.6% | −11.4% | 0.5% | −10.3% | −7.2% |
| 23 | −9.9% | 4.1% | −9.9% | −6.5% | 6.1% | −5.3% | −2.1% |
| 33.0 | −9.5% | 4.6% | −9.5% | −6.1% | 6.5% | −4.9% | −1.7% |
| 50.0 | −9.6% | 4.5% | −9.6% | −6.2% | 6.4% | −5.1% | −1.8% |
| 67.0 | −7.4% | 7.1% | −7.4% | −3.8% | 9.1% | −2.7% | 0.7% |

FIG. 14 illustrates that the adjusted estimated apparent viscosity closely approximates the apparent viscosity from the ASTM test method.

Results in a Wider Shear Rate Range

The above analysis focuses on shear rates in the range of 17-67 sec$^{-1}$. FIG. 14 shows adjusted estimated apparent viscosities obtained using the method of this invention compared to viscosities using the ASTM D-1092 test method. The multiple lines in FIG. 14 are adjusted estimated apparent viscosities obtained from Tests 1-5 above. The solid line represents the apparent viscosity using the ASTM D-1092 test method. FIG. 16 summarizes the data of FIG. 14 and extrapolates the results over a wider range of shear rates. The solid-line portion of the middle curve in FIG. 16 represents ASTM D-1092 test results based on apparent viscosity data points at 17, 23, 33, 50 and 67 sec$^{-1}$. The broken-line portions of the middle curve represent trend lines extrapolating the ASTM D-1092 test results above and below the range of 17-67 sec$^{-1}$. The graph also shows upper and lower curves representing the upper and lower limits, respectively, of the adjusted estimated apparent viscosity as determined by the method of this invention and extrapolated above and below the range of 17-67 sec$^{-1}$. It will be observed that the trend lines represented by the broken-line portions of the middle curve lie between the upper and lower curves, indicating that the adjusted estimated apparent viscosity as determined by the method of this invention closely corresponds with the extrapolated results of the ASTM D-1092 test method.

Thus, using the "Ventmeter" testers 51, 101 and test procedures of this invention, the apparent viscosities of non-Newtonian fluids at selected shear rates can be quickly calculated. Once the apparent viscosity of a particular fluid is calculated, an engineer can use this information to select the appropriate equipment to be used in a pumping system, such as systems for delivering non-Newtonian fluids to a desired location. By way of example but not limitation, the information derived by using the testing apparatus and procedures of this invention may be used to determine the size of the pump, the size of the supply line(s) for delivering fluid from the pump, the maximum length of the supply line(s), and the type of fluid to be used under given ambient conditions. Further, this information can be determined without using the ASTM D-1092 test procedure.

Figure 17:
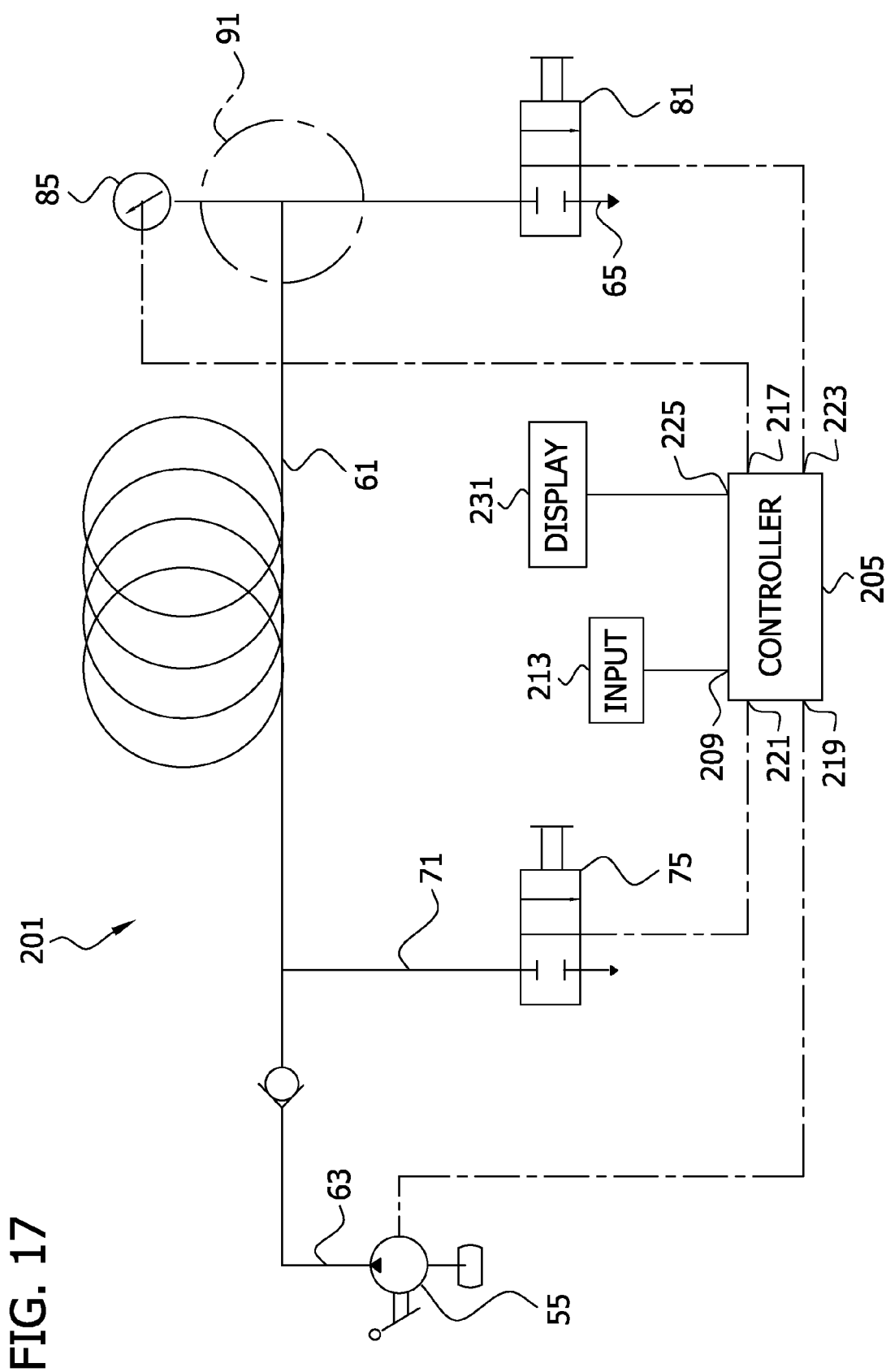
FIG. 17 is a schematic view of an automated tester used to carry out a method of this invention for estimating apparent viscosity.

FIG. 17 is a schematic illustration of another embodiment of apparatus of this invention, generally designated 201, for estimating apparent viscosity of a non-Newtonian fluid. The apparatus 201 is similar to the first embodiment and corresponding parts are designated by corresponding reference numbers. The apparatus 201 is different in that it further comprises a controller 205 having a first input 209 connected to an input device 213 (e.g., keypad or keyboard) by which a user can input information into the controller, a second input 217 connected to the pressure measuring device 85, a first output 219 for controlling operation of the pump 55, a first output 221 for controlling the operation of the venting valve 75, a second output 223 for controlling the operation of the second valve 81, and a third output 225 connected to a display 231 for displaying information relating to the test procedure.

The controller 205 is programmed to run the test procedure described above, to make the various calculations necessary to determine the estimated apparent viscosity and adjusted estimated apparent viscosity, and to record and display the results of the test. The results may be displayed visually in real time as the procedure is in progress or after the procedure is complete. The results are recorded in memory and/or printed out.

In operation, a user provides user input to the controller 205 via the input device 213. The input includes the following information:

The diameter D and length L of the tubing 61;
The selected shear rate (e.g., 67 sec$^{-1}$)
The time when the pressure measurements will be taken (e.g., t=2 sec.);
The number N of iterations of the test (e.g., N=3);
The reference shear rate $\gamma_{ref}$ (e.g., 30 sec$^{-1}$ for the highest iteration and 20 sec$^{-1}$ for the lowest iteration); and
The manner in which "n" is to be determined.

After the tube 61 is primed with the venting valve 75 closed, the controller 205 begins the process by closing the second valve 81. The controller 205 operates the pump 55 to pump fluid into the tube 61 to increase the pressure in the pressure zone 91 to about a predetermined pressure (e.g., about 1800 psig) as measured by the pressure measuring device 85. The controller then opens the second valve 81 to begin the "venting" interval. At some time t1 during the transition segment S2 of this interval (e.g., at t1=about 2 seconds), a pressure reading P is taken, as described previously. After the "venting" interval is over, the venting valve 75 is closed and the controller repeats the process N times. Desirably, the test results are recorded by a suitable recording device. The number of test runs (or iterations) "n" can be 1, 2, 3, 4 or more, and is desirably at least one. The controller then uses the collected information to calculate the adjusted estimated apparent viscosity, using formula 5 as described above, where $\gamma_{ref}$ is desirably in the range of about 20-30 sec$^{-1}$ and using n=0.3. (If only one test is run, it is recommended to use $\gamma_{ref}$=20 sec$^{-1}$.)

Alternatively, the value of "n" can be calculated by taking two pressure readings PS2 and PS3 (using the pressure measuring device 85) and using these readings in formula (12), as explained above. These pressure readings PS2 and PS3 can be based on one test or an average of multiple tests.

If more than one test is run, that is, if N is greater than 1, it is desirable (but not essential) that the pressure reading(s) (PS2 and PS3) be taken at approximately the same times during the tests. For example, if two pressure reading PS2 and PS3 are taken during each test, it is desirable that the PS2 reading be taken at the same time during all of the tests, and that the PS3 reading be taken at the same time during the tests.

The apparatus and method of this invention can be used to estimate apparent viscosity in the range of 1-150 sec$^{-1}$. The method is practical and efficient, and the method can be carried out using only the "Ventmeter" tester 55, 101 or similar apparatus which is relatively inexpensive. Unlike the previous procedure, there is no need to weigh the output of fluid from the conduit 61 during the "venting" interval. Further, using formula 5, the apparent viscosity can be easily determined at different selected shear rates. Another advantage of this method is that it allows the estimation of apparent viscosity at any shear rate value within the range of 1-150 sec$^{-1}$. Conventional test methods provide apparent viscosity values only at certain shear rates within a more limited range.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules on a tangible computer readable storage medium. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Having described aspects of the invention in detail, it will be apparent that modifications and variations are possible without departing from the scope of aspects of the invention as defined in the appended claims.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of estimating an apparent viscosity of a non-Newtonian fluid by using test apparatus, said test apparatus comprising a conduit for receiving said fluid under pressure, said conduit having an inside diameter D, a length L and a L/D ratio greater than 40, a valve system operable in a first mode to block fluid flow in the conduit to allow fluid to accumulate under pressure in a pressure zone of the conduit and in a second mode to vent the pressure zone of the conduit, and a pressure measuring device for measuring the pressure inside the pressure zone of the conduit, said method comprising:
   a) with said valve system operating in its first mode, supplying fluid under pressure to said conduit until the fluid in said pressure zone reaches a predetermined pressure;
   b) operating said valve system in its second mode to vent the pressure zone of the conduit for a predetermined time interval during which there is a transition between non-Newtonian flow and Newtonian flow;
   c) using said pressure measuring device, measuring the pressure P in said pressure zone during said transition;
   d) calculating a wall shear stress τ of the fluid based on the conduit length L, the conduit diameter D, and the measured pressure P during said transition; and
   e) determining an estimated apparent viscosity $\eta_{est}$ of the fluid at a selected shear rate using a first formula $\eta_{est}=\tau/\gamma_s$, where τ is said calculated wall shear stress and $\gamma_s$ is the selected shear rate not based on any measurement of fluid output from the conduit.

2. A method as set forth in claim 1 wherein the selected shear rate is in the range of 1 sec$^{-1}$ to 150 sec$^{-1}$.

3. A method as set forth in claim 1 further comprising determining a range of estimated apparent viscosities $\eta_{est}$ using different selected shear rates in the range of 1 sec$^{-1}$ to 150 sec−1.

4. A method as set forth in claim 1 further comprising calculating an adjusted estimated apparent viscosity $\eta_{adj}$ corresponding to an ASTM D-1092 standard using a second formula $\eta_{adj}=\eta_{est}(\gamma_s/\gamma_{ref})^n$, where $\eta_{est}$ is the estimated apparent viscosity, $\gamma_s$ is the selected shear rate, $\gamma_{ref}$ is a reference shear rate, and "n" is based on a power law relating the shear stress of the fluid to the shear rate of the fluid.

5. The method of claim 4 wherein the reference shear rate corresponds to a shear rate at which the estimated apparent viscosity $\eta_{est}$ of the fluid approximately corresponds to the apparent viscosity $\eta_a$ as measured using the ASTM D-1092 standard.

6. The method of claim 5 wherein the reference shear rate is selected from the range of about 20 sec$^{-1}$ to 30 sec$^{-1}$.

7. The method of claim 4 wherein n is about 0.3 for grease at a temperature of 72° F. and about 0.4 at a temperature of 32° F.

8. The method of claim 4 wherein n=ln(P/$P_{end}$)/ln 3, where $P_{end}$ is a measurement of the pressure in the pressure zone after the transition.

9. A method as set forth in claim 4 further comprising repeating (a)-(c) a plurality of times and, for each repetition, measuring the pressure P in the pressure zone during the transition and the pressure $P_{end}$ in the pressure zone after the transition, calculating a value for "n" for each repetition wherein n=ln(P/$P_{end}$)/ln 3, and averaging the calculated values for "n.".

10. A method as set forth in claim 1 further comprising repeating steps (a)-(e) at least two times to determine at least two estimated apparent viscosities $\eta_{esthigh}$ and $\eta_{estlow}$, $\eta_{esthigh}$ being greater than $\eta_{estlow}$, calculating an adjusted estimated apparent viscosity $\eta_{adjhigh}$ using a third formula $\eta_{adjhigh}=\eta_{esthigh}(\gamma_s/\gamma_{ref})^n$, where $\gamma_s$ is the selected shear rate and $\gamma_{ref}$ is about 30 sec$^{-1}$, and calculating an adjusted estimated apparent viscosity $\eta_{adjlow}$ using a fourth formula $\eta_{adjlow}=\eta_{estlow}(\gamma_s/\gamma_{ref})^n$, where $\gamma_s$ is the selected shear rate and $\gamma_{ref}$ is about 20 sec$^{-1}$.

11. A method as set forth in claim 10 further comprising recording $\eta_{adjhigh}$ and $\eta_{adjlow}$ as a range of estimated apparent viscosities for said fluid.

12. A method as set forth in claim 10 further comprising repeating steps (a)-(e) at least three times to determine at least three estimated apparent viscosities, and using the largest of the at least three estimated apparent viscosities to calculate $\eta_{adjhigh}$ and the smallest of the at least three estimated apparent viscosities to calculate $\eta_{adjlow}$.

13. A method as set forth in claim 12 further comprising recording $\eta_{adjhigh}$ and $\eta_{adjlow}$ as a range of estimated apparent viscosities for said fluid.

14. A method as set forth in claim 10 wherein the pressure measurement P taken during each repetition is taken at about the same time t after venting of said pressure zone is initiated.

15. A method as set forth in claim 14 wherein said time t is about 2 seconds after venting of said pressure zone is initiated.

16. A method as set forth in claim 1 wherein said valve system comprises a first valve movable between an open position and a closed position and a second valve movable between an open position and a closed position.

17. A method as set forth in claim 16 wherein the first valve is upstream from said pressure measuring device and the second valve is downstream from the pressure measuring device.

18. A method as set forth in claim 1 wherein said valve system comprises a valve having a flow orifice diameter D1 not substantially smaller than the inside diameter D of the conduit.

19. A method as set forth in claim 1 wherein said valve system comprises a valve having a flow orifice diameter D1 equal to or greater than the inside diameter D of the conduit.

20. A method as set forth in claim 1 wherein said L/D ratio is greater than 500.

21. A method as set forth in claim 1 further comprising using said estimated apparent viscosity to select equipment for a system for pumping said fluid.

22. A method as set forth in claim 1 wherein said non-Newtonian fluid is lubricating grease.

23. A method as set forth in claim 1 wherein said predetermined pressure is in the range of 1500 psig to 2200 psig.

24. A method of selecting equipment for a system for pumping a non-Newtonian fluid, comprising:
   a) providing test apparatus comprising a conduit for receiving said fluid under pressure, said conduit having an inside diameter D, a length L and a L/D ratio greater than 40, a valve system operable in a first mode to block fluid flow in the conduit to allow fluid to accumulate in a second mode to vent the pressure zone of the conduit, and a pressure measuring device for measuring the pressure inside the pressure zone of the conduit;
   b) with said valve system operating in its first mode, supplying fluid under pressure to said conduit until the fluid in said pressure zone reaches a predetermined pressure;
   c) operating said valve system in its second mode to vent the pressure zone of the conduit for a predetermined time interval during which there is a transition between non-Newtonian flow and Newtonian flow;
   d) using said pressure measuring device, measuring the pressure P in said pressure zone during said transition;
   e) calculating a wall shear stress $\tau$ of the fluid based on conduit length L, conduit diameter D, and the measured pressure P during said transition;
   f) determining an estimated apparent viscosity $\eta_{est}$ of the fluid at a selected shear rate using a first formula $\eta_{est}=\tau/\gamma_s$, where $\tau$ is said calculated wall shear stress and $\gamma_s$ is the selected shear rate not based on any measurement of fluid output from the conduit; and
   g) selecting equipment for said pumping system based at least in part on said estimated apparent viscosity $\eta_{est}$.

25. A method as set forth in claim 24 further comprising calculating an adjusted estimated apparent viscosity $\eta_{adj}$ corresponding to an ASTM D-1092 standard using a second formula $\eta_{adj}=\eta_{est}(\gamma_s/\gamma_{ref})^n$, where $\eta_{est}$ is the estimated apparent viscosity, $\gamma_s$ is the selected shear rate, $\gamma_{ref}$ is a reference shear rate, and "n" is based on a power law relating the shear stress of the fluid to the shear rate of the fluid.

26. A system for estimating an apparent viscosity of a non-Newtonian fluid comprising:
   a conduit for receiving said fluid under pressure, said conduit having an inside diameter D, a length L and a L/D ratio greater than 40;
   a valve system operable in a first mode to block fluid flow in the conduit to allow fluid to accumulate under pressure in a pressure zone of the conduit and in a second mode to vent the pressure zone of the conduit;
   a pressure measuring device for measuring the pressure inside the pressure zone of the conduit, said pressure measuring device providing a pressure signal indicative of the pressure inside the pressure zone; and a controller selectively operating said valve system in said first and second modes and receiving the pressure signal, said controller providing output information indicative of the viscosity of the fluid based on the conduit length L, the conduit diameter D, and a measured pressure P when the valve mechanism is open and the fluid transitions from non-Newtonian flow to Newtonian flow, and not based on any measurement of fluid output from the conduit.

27. The system of claim 26 further comprising a display displaying the output information.

28. The system of claim 26 wherein:
a) with said valve system operating in its first mode, fluid under pressure is supplied to said conduit until the fluid in said pressure zone reaches a predetermined pressure;
b) the controller operates said valve system in its second mode to vent the pressure zone of the conduit for a predetermined time interval during which there is a transition between non-Newtonian flow and Newtonian flow;
c) the controller calculates a wall shear stress $\tau$ of the fluid based on the conduit length L, the conduit diameter D, and the measured pressure P during said transition as indicated by the pressure signal received by the controller; and
d) the controller determines an estimated apparent viscosity $\eta_{est}$ of the fluid at a selected shear rate using a first formula $\eta_{est}=\tau/\gamma_s$, where $\gamma_s$ is said calculated wall shear stress and $\tau$ is the selected shear rate.

29. A system as set forth in claim 28 wherein the controller calculates an adjusted estimated apparent viscosity $\eta_{adj}$ corresponding to an ASTM D-1092 standard using a second formula $\eta_{adj}=\eta_{est}(\gamma_s/\gamma_{ref})^n$, where $\eta_{est}$ is the estimated apparent viscosity, $\gamma_s$ is the selected shear rate, $\gamma_{ref}$ is a reference shear rate, and "n" is based on a power law relating the shear stress of the fluid to the shear rate of the fluid.

30. A system as set forth in claim 26 wherein said valve system comprises a valve having a flow orifice diameter D1 equal to or greater than the inside diameter D of the conduit.

* * * * *